(12) United States Patent
Fonash et al.

(10) Patent No.: US 6,794,196 B2
(45) Date of Patent: Sep. 21, 2004

(54) DEPOSITED THIN FILMS AND THEIR USE IN DETECTION, ATTACHMENT AND BIO-MEDICAL APPLICATIONS

(75) Inventors: Stephen J. Fonash, State College, PA (US); Sanghoon Bae, State College, PA (US); Daniel J. Hayes, State College, PA (US); Joseph Cuiffi, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/739,940

(22) Filed: Dec. 19, 2000

(65) Prior Publication Data

US 2002/0048531 A1 Apr. 25, 2002

Related U.S. Application Data

(63) Continuation-in-part of application No. 09/580,105, filed on May 30, 2000, now Pat. No. 6,399,107.
(60) Provisional application No. 60/172,840, filed on Dec. 20, 1999, provisional application No. 60/201,936, filed on May 5, 2000, provisional application No. 60/201,937, filed on May 5, 2000, and provisional application No. 60/231,474, filed on Sep. 8, 2000.

(51) Int. Cl.$^7$ ............................ G01N 1/00; G01N 27/00
(52) U.S. Cl. ....................... 436/174; 436/149; 436/151; 435/287.1; 435/287.8
(58) Field of Search .......................... 435/4, 7.2, 287.1, 435/287.7, 287.8, 288.6; 422/68.1, 82.01, 82.05; 436/149, 151, 174

(56) References Cited

U.S. PATENT DOCUMENTS

| | | | | |
|---|---|---|---|---|
| 4,384,957 A | * | 5/1983 | Crowder et al. | 210/198.2 |
| 5,552,272 A | * | 9/1996 | Bogart | 435/6 |
| 5,605,798 A | * | 2/1997 | Koster | 435/6 |
| 5,658,732 A | * | 8/1997 | Ebersole et al. | 422/68.1 |
| 5,705,813 A | * | 1/1998 | Apffel et al. | 250/288 |
| 5,716,825 A | * | 2/1998 | Hancock et al. | 435/286.5 |
| 5,719,060 A | * | 2/1998 | Hutchens et al. | 436/174 |
| 5,955,729 A | * | 9/1999 | Nelson et al. | 250/282 |
| 6,288,390 B1 | * | 9/2001 | Siuzdak et al. | 250/288 |
| 6,319,469 B1 | * | 11/2001 | Mian et al. | 422/64 |

OTHER PUBLICATIONS

Bal et al., "Matrix–Assisted Laser Desorption/Ionization Using an Active Perfluorosulfonated Ionmer Film Substrate", 1994, Ana Chem., 66:3423–3430.*
Farmer et al., Determination of Protein Interactions by Matrix–assisted Laser Desorption/Ionization Mass Spectrometry 1998, J. Mass Spectrometry, 33:697–704.*
Farmer et al., Determination of Protein–Protein Interactions by Matrix–assisted Laser Desorption/Ionization Mass Spectrometry, 1998, J. Mass Spectrometry, 33:697–704.*
Dale et al., Graphite/Liquid Mixed Matrices for Laser Desorption/Ionization Mass Spectrometry, Anal. Chem., 1996, 60(19):3321–3329.*
Uhlir, Jr. "Electrolytic shaping of Geranium and Silicon." Bell Syst. Tech. J. 35, 333–347 (1956).
Watanabe et al. "Application of a thick anode film to semiconductor devices." Review of Electrical Communication Laboratories, vol. 19, No. 7–8, Jul.–Aug. 1971.
Anderson et al. "Porous Polycrystalline Silicon: A new material for MEMS." J. of Microelectromechanical Systems, vol. 3, No. 1, Mar. 1994.
Messier et al. "Black a–Si solar selective absorber surfaces." J. Appl. Phys. 51(3), Mar. 1980.
Canham. "Silicon quantum wire array fabrication by electrochemical and chemical dissolution of wafers." Appl. Phys. Lett. 57(10), Sep. 3, 1990.
Schechter. "Gas sensing properties of porous silicon." Anal. Chem. 1995, 67, 3727–3732.
Wei et al. "Desorption–ionization mass spectrometry on porous silicon." Nature, vol. 399, 243–246, May 20, 1999.
Canham et al. "Calcium phosphate nucleation on porous silicon: factors influencing kinetics in acellular simulated body fluids." Thin Solid Films 297 (1997) 304–307.
Steiner et al. "Micromachining applications of porous silicon." Thin Solid Films 255 (1995) 52–58.
Fonash et al. " Nanostructured silicon for Bio–medical applications." Nanofabrication Facility, 189 MRI Building, The Pennsylvania State University, University Park, PA 16802.
Hayes et al. "Desorption–ionization mass spectrometry using deposited nanostructured silicon films." Anal. Chem. 2001, 73, 1292–1295.
Shen et al. "Porous silicon as a versatile platform for laser desorption/ionization mass spectrometry." Anal. Chem. 2001, 73, 612–619.
Kruse et al. "Experimental factors ontrolling analyte ion generation in laser desorption/ionization mass spectrometry on porous silicon." Analytical Chemistry. Published on the Web.

* cited by examiner

*Primary Examiner*—Andrew Wang
*Assistant Examiner*—My-Chau T Tran
(74) *Attorney, Agent, or Firm*—Perkins Smith & Cohen LLP; Peter J. Borghetti; Orlando Lopez

(57) ABSTRACT

The present invention is directed to the use of deposited thin films for chemical or biological analysis. The invention further relates to the use of these thin films in separation adherence and detection of chemical of biological samples. Applications of these thin films include desorption-ionization mass spectroscopy, electrical contacts for organic thin films and molecules, optical coupling of light energy for analysis, biological materials manipulation, chromatographic separation, head space adsorbance media, media for atomic molecular adsorbance or attachment, and substrates for cell attachment.

19 Claims, 25 Drawing Sheets

DEPOSITED THIN FILMS AND THEIR USE IN DETECTION, ATTACHMENT AND BIO-MEDICAL APPLICATIONS

This application is a continuation-in-Dart of U.S. Ser. No. 09/580,105 filed May 30, 2000, now U.S. Pat. No. 6,399,107; and claims the benefit of U.S. Provisional Application No. 60/172,840 filed Dec. 20, 1999; U.S. Provisional Application No. 60/201,936 filed May 5, 2000; U.S. Provisional Application No. 60/201,937 filed May 5, 2000; and U.S. Provisional Application No. 60/231,474 filed Sep. 8, 2000.

U.S. Provisional Application No. 60/172,840 filed Dec. 20, 1999 was made with government support under the grant F33615-98-1-5166 415-37; 773A from the Defense Advanced Research Projects Agency. Accordingly, the U.S. Government has certain rights in the invention.

BACKGROUND OF THE INVENTION

1. Field of the Invention

The present invention is directed to deposited thin films of semiconductors and dielectrics. The present invention further relates to the use of these thin films in detection, analytical, contact, and biomedical applications. Applications of these thin films include desorption-ionization mass spectroscopy, electrical contacts for organic thin films and molecules, optical coupling of light energy for analysis, biological materials manipulation, chromatographic separation, head space adsorbance media, media for atomic molecular adsorbance or attachment, and substrates for cell attachment.

2. Description of Related Art

There is a great deal of interest in semiconductor and semiconductor-based (e.g., oxides, nitrides) materials with large surface to volume ratios; i.e., with large surface area. The reasons for this are two-fold. First, because of the large surface area, such materials are open to widespread surface chemical attack and, therefore, can be used as separation or release layers. These are needed in a variety of applications including MEMS (microelectro-mechanical devices), interconnect dielectric, micro-sensor, micro-fluidic and wafer separation applications. Secondly, these materials can be used as cell and molecule attachment layers, contacts and sensor materials. In addition, such materials can be very compatible with microelectronics. There are various approaches to producing large surface to volume (i.e., large surface area) materials. The technique attracting the most attention today is based on electrochemical etching. When electrochemical etching is used to produce large surface area silicon, the resulting material is commonly termed porous silicon. Porous Si was first obtained in 1956 electrochemically by Uhlir [A. Uhlir, Bell Syst. Tech. J. 35, 333 (1956).] at Bell Labs but it was not until 1970 that the porous nature of the electrochemically etched Si was realized [Y. Watanabe and T. Sakai, Rev. Electron. Commun. Labs. 19, 899 (1971). Recent discussions can be found in R. C. Anderson, R. C. Muller, and C. W. Tobias, Journal of Microelectromechanical System, vol. 3, (1994), 10.

The starting material for this wet etched conventional porous Si material is either conventional silicon wafers or thin film Si produced by some deposition process such as low pressure chemical vapor deposition (LPCVD) or plasma enhanced chemical vapor deposition (PECVD). In the electrochemical wet etching process the sample is exposed to a wet solution and a current is passed through a contact to the etching sample, through the etching sample, through the solution (e.g., a mixture of hydrofluoric acid, water and ethanol), and through an electrode contacting the solution (the cathode; e.g., platinum). This current causes the "pitting" or etching of the Si producing a porous network structure.

In the electrochemical (anodic) etching process the structure (e.g., pore size and spacing) and the porous-Si layer thickness are controllable by the resistivity of the silicon itself (magnitude and type), current density, applied potential, electrolyte composition, application of light, temperature, and exposure time. For sufficiently long exposures and for sufficiently thick starting material, this electrochemical etching process can be continued to the point where nanoscale structure (i.e., features of the order of nanometers) is obtained. The silicon features are a continuous single crystal when the sample is etched from a single crystal wafer, as is usually done, or polycrystalline silicon when the sample is etched from a deposited film. All these conventional (electrochemically etched) porous silicon materials are distinguished by (1) being the result of a wet, electrochemical etching process, (2) requiring a contact on the sample during this wet etching, (3) having generally disconnected pore regions which can be connected after extensive etching, and (4) being the result of a sequential processing first necessitating formation of the silicon and then necessitating subsequent wet etching. Besides the complexity of having to prepare, use, and dispose of wet chemical etching baths, these wet etched porous materials suffer from a problem of residual etching species and products remaining in the pores.

An alternative approach to producing a porous silicon thin film was shown by Messier (R. Messier, S. V. Krishnaswamy, L. R. Gilbert, and P. Swab, J. Appl. Phys. 51, 1611 (1980).). In this approach, a film with a spatially varying density was deposited. This film was subsequently wet etched, which removed at least some of the low-density region. As a result of this wet etch step, there was an increase in the film surface to volume ratio.

Intense research activity in porous semiconductors has been stimulated over the last decade by the discovery of room temperature visible light emission from electrochemically prepared porous Si in 1990 by Canham (L. T. Canham, Appl. Phys. Lett. 57, 1046 (1990)). Soon after Canham's discovery, further intriguing properties of electrochemically prepared porous silicon were also realized, such as gas sensitivity, bio-compatibility and ease of micromachining, etc. (I. Schecter et al., Anal. Chem. 67, 3727 (1995); J. Wei et al. Nature 399, 243 (1999); L. T. Canham et al., Thin Sold Films, 297, 304 (1997); P. Steiner et al., Thin Solid Films 255, 52 (1995)). All these demonstrated applications to date have been based on the porous silicon material produced by electrochemically etching a wafer or deposited film of silicon.

The approach to producing a high surface area to volume ratio material in the present invention is to use deposition to grow as-deposited high surface-area films. In fact, we show that, with careful control of deposition parameters and techniques, we can attain a spectrum of films with tunable, surface area to volume ratios. This tunability allows morphology from continuous (surface area is the film area; i.e., void free) films to materials with up to about 90% porosity. We show such films have tunable chemical and physical properties such as variable species adsorption, light reflectance, and light absorption properties. Depending on the deposition technique and parameters, these thin films may be continuous (void free) or may have voids between columns and clusters. The present approach uses deposition performed at low temperature and tailored to attain the required morphology. There is no specific etching step involved and no wet processing. The present inventors have demonstrated that the present invention can be used to control void size and void fraction, that a columnar/void network morphology can be produced and that the columns can be polycrystalline material. In the demonstrations provided here for these controlled morphology films, plasma enhanced chemical vapor deposition (PECVD) is used to give continuous (void free) films, physical vapor deposition (PVD) is used to give an intermediate morphology, and PECVD is used to produce high void density (high surface area) material. Due to the deposition approach, high porosity (of up to approximately 90%) is attainable in the high void density material without any specific etching step. None of the controlled morphology films of this invention requires contacts, wet processing, or both. Also unique to the present invention is its ability to fabricate these deposited films, with designed morphology matched to the application, on various types of substrates including glass, metal foils, insulators, plastic, and semiconductor-containing materials including substrates with circuit structures.

As noted, the high void density morphology material is demonstrated using PECVD. In particular a this columnar/void network silicon was demonstrated by use of a high density plasma tool (e.g., Electron Cyclotron Resonance Plasma Enhanced Chemical Vapor Deposition (ECR-PECVD) tool (PlasmaTherm SLR-770)) using hydrogen diluted silane ($H_2$:$SiH_4$) as the precursor gas at substrate deposition temperatures less than or equal to about 250° C. This tool plays off silicon etching and deposition to create a two-dimensional silicon array and analysis has demonstrated that silicon column size is controllable and the spacing between columns is controllable. The resulting columnar/void network structure is nanoscale in feature size and fully developed after a film thickness in the range of 10–20 nm is established. This enables the direct deposition of high porosity crystalline or amorphous silicon on any substrate and at any thickness greater than about 10 nm. The columnar/void semiconductor films produced by the present invention may be converted to insulators or metallic compounds through in situ or ex situ processing. In addition, other layers such as anti-reflective (AR) coatings or functionalizing layers may be deposited after or before deposition of the columnar/void network material. By varying the deposition parameters in a high-density plasma tool, either continuous (void free) intermediate, or high void density material may be produced.

As noted, the prior art contains two approaches to creating porous silicon: (1) wet electrochemical etching of deposited silicon or of silicon wafers to produce a porous silicon with a "coral-like" morphology of polycrystalline or single-crystal silicon "fingers" or (2) deposition to produce a material of varying density amorphous silicon followed by wet etching. The former material is the subject of a great deal of research and development activity. However, it requires wet chemical etching for its formation. The latter material suffers from only being demonstrated in the amorphous phase, from having a morphology that varies with thickness, and from requiring wet etching to control void density. Since its "voids" are believed to be lower material density regions, as opposed to true voids, it requires this subsequent wet etching for true void tailoring and control. The high surface area to volume ratio silicon of this invention requires no wet processing due to its nanoscale features and voids. It has a fully controllable morphology and porosity and can be in the polycrystalline or amorphous phase as desired.

This invention is the creation of controllable and tailorable surface area films from continuous films (no voids) to high surface area to volume ratio films (high void density) by deposition at low temperatures. The film morphology (surface area to volume ratio) is tailored to the film use. These materials are particularly suitable for deposition on glass, plastic or substrates requiring low processing temperatures such as substrates containing previously formed sensor, electronic or opto-electronic devices and circuits. Due to the wide, demonstrated void volume range possible for the materials of this invention, they can be used for a number of applications including sensing, airgaps (optical mixing, microfluidics, molecular sorting, low dielectric constant structures, etc.), fixing and electrically contacting molecules and cells, and molecular desorption applications.

SUMMARY OF THE INVENTION

The present invention is directed to deposited film structures having morphologies that are variable and tailorable from a continuous film (no voids) to a film comprising: (a) a network of columnar-like units in a continuous void; and (b) a substrate to which the network of columnar-like units is adhered. These films are based on chemical elements such as silicon, germanium, carbon, hydrogen or mixtures thereof. In a preferred embodiment, the substrate supporting these films is composed of a material such as glass, metal, ceramic, insulation material, plastic material, silicon or semiconductor-containing material. This invention covers the use of deposited AR films on these deposited films for enhancement of light coupling. Table 1 summarizes the deposited variable morphology films of this invention and some examples of morphology-applications tailoring.

TABLE I

Deposited Films of this invention, their Morphology, and some Morphology-Applications Tailoring

| Deposited Film | Morphology | Some Morphology-Applications Matches |
|---|---|---|
| Deposited Continuous Films of this Invention | No voids | Lack of voids means little adsorption of ambient substances. Ideal for desorption spectrometry applications where ambients such as hydrocarbons need to be avoided |
| Deposited Column Structure Films of this Invention | Void regions present Morphology is between continuous film and nanostructured columnar/void network film | Low void density means little adsorption of ambient. Useful in desorption spectroscopy applications where analyte adsorption and/or application is enhanced over continuous film but ambient adsorption is not as extreme as in columnar/void network material. In general, film has properties between continuous film and nanostructured columnar/void network material |
| Deposited Columnar/Void Network Films of this Invention | By varying pressure and power)in mTorr regime in a high density plasma tool, for example, porosity can be varied between 0% to about 90% | Columns can be used for contacts Morphology used for steric functions Adsorbs ambient species readily for monitoring Low UV reflectance possible High optical absorption Quantum size effects can be present High surface area is advantageous for the adsorption of analyte molecules, cells, and species from drops |

The films of this invention are deposited at low temperatures and are morphologically tailored for specific applications, examples of which are noted in Table 1. In an embodiment of this invention the material is a continuous semiconductor film having no voids and deposited by PECVD. In an embodiment of this invention the material has an intermediate morphology with a low void density and is deposited by PVD. In an embodiment of the invention, the films are a nanostructured columnar/void material with a network of units collected in clusters and formed by deposition via a high-density plasma. In this latter case, the spacing and height of the network of columnar-like units are adjustable by variables including oxidation, silicidation, etching, voltage, current, voltage between plasma and substrate, substrate temperature, plasma power, process pressure, electromagnetic field in the vicinity of the substrate, deposition gases and flow rates, chamber conditioning, and substrate surface. Furthermore, by using the latter methodology and modifying the deposition conditions, not only can the nanostructured columnar/void material be deposited, but also the mentioned continuous and low void density films can be produced.

The present invention is also directed to a method for detection of analytes in a sample. The method for the analysis of a sample comprises (a) applying the sample to a deposited thin-film; and (b) analyzing the sample by a detection means. More particularly, the method comprises: (a) selecting one of the film morphologies of Table 1, as dictated by the specific application, (b) applying the analyte onto the selected film structure described above; (c) transferring the sample into a detection device; (d) discharging light such as laser energy on the sample, thereby transforming the analytes in the sample into charged particles which detach from the film structure enter a vacuum having an electric field and move through the detection device or detection means to a detector. The sample to be selected, includes organic chemical compositions, inorganic chemical compositions, biochemical compositions, cells, microorganisms, peptides, polypeptides, proteins, lipids, carbohydrates, nucleic acids, or mixtures thereof. The peptide, polypeptide, or protein sample has a molecular weight greater than 0 Daltons. The sample is directly applied to the film as a liquid and thereafter evaporated to dryness. And, the sample is in aqueous or organic solution or suspension.

The criteria for selecting a particular film is based on properties of the film such as laser-light reflection, optical absorption, species absorption, and ambient absorption. The selection of deposited thin-films which are used for the above method includes continuous film, a column structure film, a columnar-void film, and a mixture thereof. The film is essentially a single homogenous film or a heterogeneous mixture of more than one film. The heterogeneous mixture is a patterned columnar void network of films.

The analyte may be applied by an application/removal protocol for such application, which is also the subject of this invention. Application of sample to a film is either by (1) adsorption from a solid, liquid or gas; or (2) direct application to the surface of the deposited thin film as a solid or liquid. In an embodiment of the invention, the sample is applied to the film directly from a chemical separation means including liquid chromatography, gas chromatography, and deposited thin-film chromatography.

In one embodiment of the invention, the detection means or detection device for the above method includes light desorption mass spectroscopy, antigen-antibody reaction detection, fluorescence detection means, optical detection means, radioactivity detection means, electrical detection means, chemical detection means, antigen-antibody reaction detection and combinations thereof. The chemical detection means involves dye or coloring means and colorimetry or visualization. Preferably, the detection device uses time of flight analysis for species identification. These films and the morphology selection and tailoring outlined above may also be used for a means of chemical separation such as chromatography.

The film morphology selection is based on the properties needed for the application. For example, in applications where sample confinement is an issue, the spacing and height of the network of columnar-like units of the columnar/void network morphology film structure may be adjusted to reduce lateral drop spreading of the analyte. The film structure is selected from Table 1 as needed, based on one or more film attributes: low laser-light reflection (which may also include the use of AR coatings), strong optical absorption, species adsorption, and ambient adsorption. The method for separation of analytes in a sample using a chemical separation means comprising a deposited thin film, the method comprising the steps of: (a) applying the sample to the deposited thin film; (b) passing the sample through the deposited thin film; whereby the analytes of the sample migrate through the deposited thin film thereby separating each analyte in the sample by mobility of each analyte. Forces for the passing of the sample in step (b) include gravity, centrifugal force, electric field, and pressure gradient. More particularly, the present invention is directed to a method for separation of analytes in a sample comprising: (a) exposing the analyte to the film structure as described above; and (b) moving the sample through the film structure whereby the analytes of the sample migrate through the network of columnar-like units of the film structure thereby separating each analyte in the sample by properties such as the mobility of each analyte. The mobility of each analyte is dependent upon mass, charge to mass ratio, physical interaction, size, or shape. The spacing and height of the network of columnar-like units of the film structure is adjusted to control the migration of targeted analytes.

The present invention is also directed to a method for selective adherence of analytes in a sample comprising the steps of: (a) modifying, functionalizing or patterning in a physical or chemical manner the deposited thin-film; and (b) applying the sample to a deposited thin-film, whereby a particular analyte or analytes from the sample adhere to the deposited thin-film. More particularly, the present invention is directed to a method for selective adherence of the analytes of a sample comprising: (a) modifying the film structure described above such that specific regions have been physically shaped or chemically functionalized to capture analyte; and (b) exposing the sample to be analyzed to the film structure whereby particular analytes in the sample adhere onto the film structure in pre-specified regions. The analyte-containing sample may be in solid, gaseous or liquid form. A surface of the film structure of step (a) may be functionalized with a molecule or molecules including: reactive, non-reactive, organic, organo-metallic and non-organic species, thereby allowing the surface to be specified for reaction with particular analytes. The surface of the film may be physically defined; for example, a hole, receptacle, or confining pattern created by a subsequent functionalization, surface treatment, molecular attachment or film deposition may be defined to segregate analyte to specific regions of the film. Chemical modification to the film structure may comprise steps such as oxidation, reduction, addition of a chemical element, hydophobicity or hydrophylicity treatments, lipid attachment, Lewis acid mediated hydrosilylation, or silicidation. In one embodiment of the invention, the film is patterned by lithography of the film or of a subsequently positioned material. In another embodiment of the invention, the film is modified to adhere an antibody, antibodies or other chemical moiety, with the sample. A detection means is then used to detect antigen-antibody reaction or the adherence of the antibody, antibodies or other chemical to the film. In a further embodiment of the invention, the film is modified to adhere cells including neuronal, glia, osteoblasts, osteoclasts, chondrocytes, kerotinocytes, melanocytes, and epidermal cells; whereby the cells proliferate on the film. In a further embodiment of the invention, the film is modified to adhere cells including neuronal, glia, osteoblasts, osteoclasts, chondrocytes, kerotinocytes, melanocytes, and epidermal cells; whereby the cells proliferate on the film. The film can be modified so that cell proliferation is controlled or restricted. Also, the film with cells adhered can be placed in vivo.

The present invention is also directed to a method for determining a property of a particular analyte in a sample comprising: (a) modifying a first film structure; (b) modifying a second film structure; (c) applying a sample to the first and second film structures; and (d) analyzing the first and second film structures to determine which film structure interacted with the particular analyte in the sample. It is one embodiment of the invention, whereby the first and second film structures are separately modified by various treatments such as attachments or Lewis acid mediated reactions on the surface of the first and second film structures.

The present invention is directed to a method for specifying a particular reaction comprising the steps of: (a) functionalizing the film; (b) applying a sample with multiple analytes to the functionalized film; wherein a particular analyte in the sample reacts in the presence of the functionalized film. The chemical property of a particular analyte can be determined using the above described method. In one embodiment of the invention, the first molecule adheres to the film structure in a specified orientation. In another embodiment of the invention, the second molecule is selected from the group including: nucleic acids, proteins, organic and organo-metallic reagents. In a further embodiment of the invention, the first molecule adheres to the film structure in a specified orientation and the second molecule reacts with the first molecule.

The present invention is directed to a method for screening a library of samples comprising the steps of: (a) applying each sample in the library of samples to a deposited thin film; and (b) analyzing each sample by a detection means. In one embodiment of the present invention is further directed to a method for screening a library of compounds to identify a particular characteristic in the compounds comprises: (a) modifying a film structure as described above; (b) applying a compound to the film structure; (c) analyzing the film structure with the compound; and (d) comparing analysis of the film structure with compound to the film structure without the compound so as to determine whether a reaction has taken place.

The present invention is directed to a method for promotion of cell analysis, cell products, and/or cell growth comprising: (a) modifying the surface and structure of the film structure as described above; and (b) exposing a sample to the film structure; whereby particular cells in the sample adhere onto the film structure and wherein the particular cells proliferate on the film structure. In one embodiment of the invention, the cells are selected from the group including: neuronal, glia, osteoblasts, osteoclasts, chondrocytes, kerotinocytes, melanocytes, and epidermal cells. The film structure may be modified in step (a) so that the cell growth is controlled or restricted. The sample (film structure with cells) may be placed in vivo.

Using these films for molecular attachment may also be explored for producing contacts to organic semiconductors and molecules used in molecular electronics. Such films can be excellent contacts due to the carrier injection capabilities of semiconductors or due to their use as silicides with their specific potential for high conductivities.

DETAILED DESCRIPTION OF THE INVENTION

Figure 1:
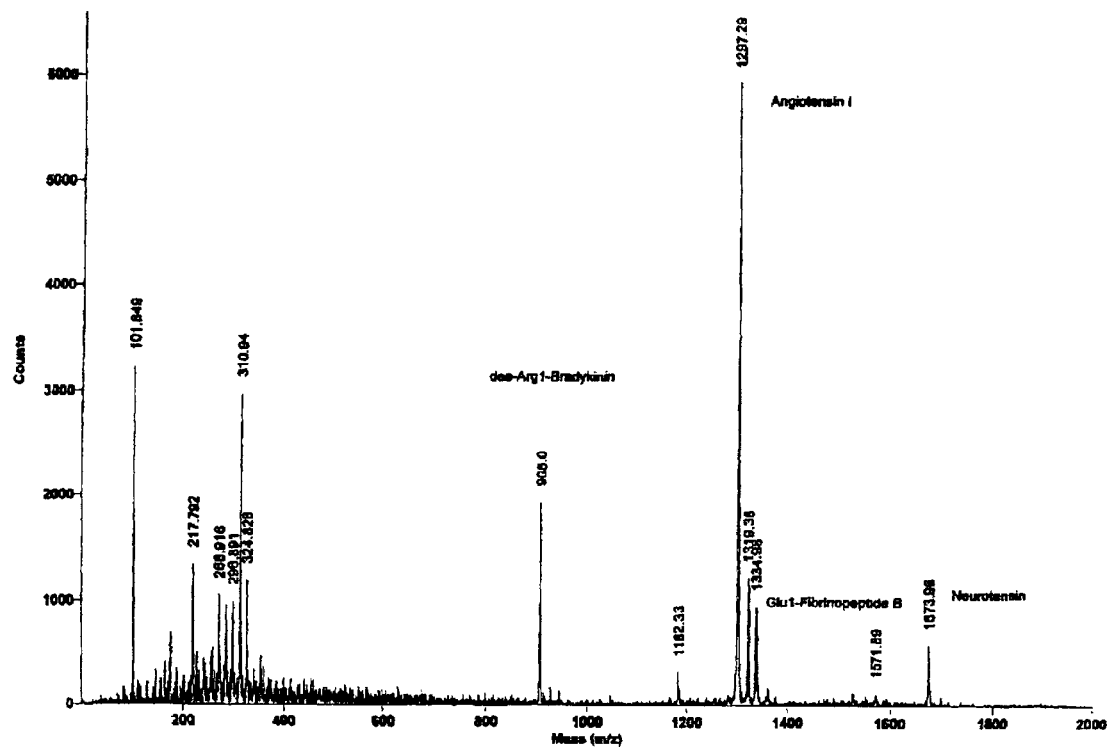
FIG. 1 is a graph plotting peptides detected (with no matrix) using the columnar/void network thin film silicon substrate of Table 1 against mass/charge (m/z).

The present invention demonstrates the tailoring of the morphology of semiconductor films, deposited at low temperatures on a variety of substrates including glass and plastics, to applications including mass spectroscopy, contacts, and separation technologies such as chromatography. The present invention shows how to obtain continuous, medium void content, and high void content film morphologies, outlines the need to tailor these films to specific applications, and provides a methodology for matching morphology to application. While various deposition techniques can produce different types of morphologies, the high-density plasma approach can produce all three by varying the deposition parameters.

(1) The Thin Films

Continuous (no voids) Morphology Semiconductor Films

The continuous film (no voids) semiconductor material of Table 1 is demonstrated herein using PECVD. These films are distinguished by having no void structure at all. As a consequence their optical properties and species adsorption properties are essentially the same as bulk material. That is, silicon films of this morphology have the species adsorption properties, optical reflectance, optical absorption, and analyte adsorption properties of a silicon wafer. These materials are particularly suitable for deposition on glass or plastic or substrates requiring low processing temperatures such as substrates containing previously formed sensor, electronic or opto-electronic devices and circuits.

The medium morphology (column) material of Table 1 is demonstrated herein using PVD material. These films have a void structure but it does not significantly reduce optical reflectance. Further, this intermediate void structure does facilitate some ambient species adsorption but laser desorption mass spectrometery characterization shows this to be intermediate between that of the continuous film and the columnar/void network film. Laser desorption mass spectrometery also shows the analyte adsorbing abilities of this morphology to be intermediate between that of the continuous film and the columnar/void network film. These materials are particularly suitable for deposition on glass or plastic or substrates requiring low processing temperatures such as substrates containing previously formed sensor, electronic or opto-electronic devices and circuits.

Columnar/void Network Morphology Semiconductor Films

The columnar/void network material of Table 1 is demonstrated using PECVD. These columnar/void network films provide the highest surface area to volume ratios (highest void content) and they are demonstrated using the specific case of a high-density plasma approach. This approach results in simultaneous plasma deposition and etching to obtain high surface to volume crystalline or amorphous semiconductor thin films. All dry processing is used in the film formation and no wet processing need be involved. With proper conditioning of the processing chamber, proper preparation of the substrate, and proper selection of the deposition parameters, these films always have a controllable and adjustable columnar/void network morphology with interconnected voids (pores) and columns approximately normal to a substrate perpendicular to the impinging flux. In the case of the other extreme situation, (when a surface is parallel to the impinging flux), our columnar/void material displays a morphology with columns at an angle to the surface which is not necessarily perpendicular but is defined and orderly. We know of no other deposited film capable of this columnar structure on a vertical surface.

Unlike conventional porous silicon which is produced by wet etching or films produced by deposition followed by etching, this interconnected void network of our columnar/void network films is present after deposition and is found in any columnar/void network film of thickness greater than about 10 to 20 nm. Unlike conventional porous silicon, our columnar/void network films may or may not be doped. Also, unlike conventional porous silicon, the columnar/void network materials of the present invention can be produced on a variety of substrates, such as, glass, metal foils, and plastics, as well as on the more conventional substrates, such as, silicon wafers. As an example, silicon films made using an ECR high density plasma (HDP) tool were used to demonstrate this approach of deposited high surface area to volume ratio films. The experiment also established visible luminescence, gas sensitivity, airgap structure formation, desorption mass spectroscopy, etc. for the resulting columnar/void network material. The present invention is demonstrated with a deposited material with distinct interconnected void arrangement, oriented columns and uniform nanostructure, low temperature processing, and a unique process exploiting the advantages of plasma deposition technology offering many new possibilities unhindered by the need for wet processing, wet etching, or both. In addition, the relatively thick starting material needed in the conventional porous approach based on electrochemical etching to obtain small feature sizes is avoided. The columnar/void network material of this invention also has a number of technological and economical advantages compared to the conventional porous silicon fabrication techniques.

Our approach to deposited columnar/void materials is demonstrated using a simultaneous plasma etching/deposition technique producing films that can be deposited at very low temperatures, can have amorphous or polycrystalline columns, have high density levels of porosity (up to 90%), can have doped or un-doped columns, and are very controllable allowing void (i.e., pore) size to be tailored to an application. Since the process temperatures during the film depositions are very low (i.e., room temperature to approximately 250° C.), the technique places no restriction on substrates. The special attributes of the deposited columnar/void network-type of silicon (i.e., a morphology arrangement having columns oriented with respect to the transition layer and penetrating through a continuous void) are controlled by a number of factors. For this demonstration of a deposited columnar/void material, these include the (a) voltage between plasma and substrate, (b) substrate temperature, (c) plasma power and process pressure, (d) magnetic field in the vicinity of the substrate, (e) deposition gases and flow rates, (f) chamber conditioning, and (g) substrate surface. The influence of a number of these factors is not what would be expected.

These materials are particularly suitable for deposition on glass or plastic or other substrates requiring low processing temperatures such as substrates containing previously formed sensor, electronic or opto-electronic devices and circuits. Due to the demonstrated wide porosity range possible for the materials of this invention, they can be used for a number of applications including light (laser) desorption-ionization mass spectrometry for molecules and cell contents, optical coupling of light energy for molecular analysis, improved contacts for carrier injection efficiency and enhanced definition of deposited organic materials, cell growth, substrates for cell products, biological materials manipulation, as well as many other applications.

(2) Light (Laser) Desorption-Ionization

Analysis of molecules and compounds using mass spectroscopy has proven very effective in many fields. Typically, mass spectrometry involves performing a "time of flight" analysis by electrically accelerating ionized species through a distance under vacuum and detecting their travel times. From this information, a very precise mass spectrum can be produced, providing a useful compositional representation of the sample. Throughout the last 20 years, the major developments in mass spectrometry have come from the various methods of producing the ionized/gaseous form of the sample, necessary for the "time of flight" measurement. Techniques range from evaporation to ion beam bombardment, and each is useful for specific sample types. A particularly useful approach has proven to be provided by laser desorption mass spectroscopy.

Matrix-assisted laser desorption/ionization (MALDI) is the most common "time of flight" technique used today and is currently limited by the signal noise introduced by the matrix itself. In the MALDI approach, first the molecular solution to be analyzed is mixed, typically having the molecular constituents in a water base, into an organic resin, which is placed on a sample plate and allowed to solidify. The sample plate, which can hold a number of samples, is loaded into a vacuum chamber where the "time of flight" analysis is performed. An organic matrix on a substrate, holds the molecular species to be detected while acting as an energy absorber. A laser then impinges on the matrix-analyte mixture, and, when the matrix absorbs the laser energy, it vaporizes. The resulting desorbed molecules, which include the analyte and matrix components, are then mass analyzed. Matrix material molecules add to the collected signal, however, preventing the detection of smaller molecules. The inclusion of the matrix molecules into the collected signal limits the low mass detection of this method to above 500 amu, but it has proven to be effective for analyzing a large range of molecules up to approximately 100,000 amu. Besides low mass and noise limitations, further downfalls of this system lie in the sample preparation itself, because the matrix/sample mixture requires experienced chemical handling, usually requires time-consuming drying, and has throughput limitations for large scale clinical applications. For all of these reasons, the development and use of a non-matrix method is quite appealing and has attracted a significant research effort.

Obtaining mass spectra for synthetic and biological samples using matrix assisted laser desorption ionization (MALDI) mass spectrometry offers soft ionization capabilities that preserve molecular mass information over a broad molecular mass range. These features have made MALDI a popular technique since its inception. However, for analysis of low mass analytes (<m/z 500), irreproducible and heterogeneous cocrystallization, suppression of ionization by electrolytes and other additives, and interference from matrix ions have limited the utility of MALDI in automated high-throughput combinatorial and chip-array analyses. Because of its limitations MALDI has not been very successful in direct analysis of cells and cell material. Active efforts to improve this process has led to successful desorption ionization from particles suspended in a liquid such as glycerol. More recently, desorption ionization was achieved without the use of a matrix from electrochemically etched conventional porous silicon. This matrix-less approach, which has drawn considerable attention, utilized a porous silicon support material that is electrochemically etched from bulk silicon wafers.

The component of the present invention dealing with light (laser) desorption for mass spectrometry is a matrix-less laser desorption approach. It uses the deposited semiconductor films of Table 1. Film selection is tailored for specific situations. It is a unique thin film substrate approach with benefits over both matrix desorption and the matrix-less approach based on wet-etched, porous silicon substrates. This invention shows how to obtain the various semiconductor film morphologies needed and how to tailor for specific mass spectrometry applications using these deposited semiconductor films as substrates. The tailored substrate types of this invention include (1) continuous semiconductor films useful, for example, when background adsorbing of ambients must be suppressed, light reflection can be tolerated, and low analyte yield can be compensated by higher light intensity (2) column structure films useful, for example, when some background adsorbing of ambients must be suppressed but some enhanced adsorption and drying-control of analyte is desired, and (3) deposited thin film nanostructured columnar/void semiconductors useful for their suppressed reflectance, high species adsorption, high optical absorption, analyte application and drying control, and even quantum size effects such as enhanced optical absorption. The specific demonstrations of this invention use PECVD continuous films, PVD medium morphology (column) films, and high-density plasma PECVD nanostructured columnar/void network films. All three morphologies can be obtained with the high-density plasma approach by varying the deposition parameters. The films used in these demonstrations varied in thickness from 500 Å to 5 microns. In the case of molecular detection, the sample peptides used as the analyte for the demonstrations were transferred to the film using the usual drying approach of MALDI or using a unique approach, which is part of this invention. In the latter case they were applied in solution (water was used in these demonstrations) and the excess was systematically removed by suction. This unique application/ excess-removal approach, possible when using the column morphology or columnar/void network morphology substrates, gives a systematic, high-throughput methodology for analyte positioning.

Figure 2:
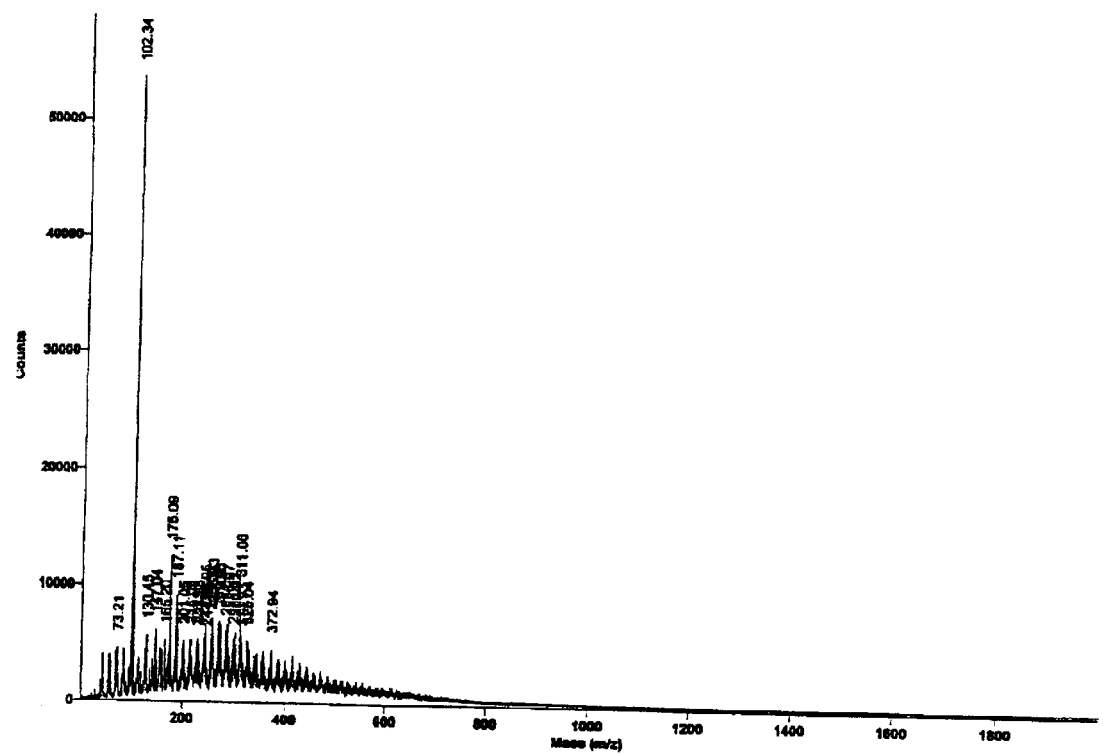
FIG. 2 is a graph-plotting signal received from the columnar/void network thin-film silicon substrate of Table 1 without deposited peptides against mass/charge (m/z).
Figure 3:
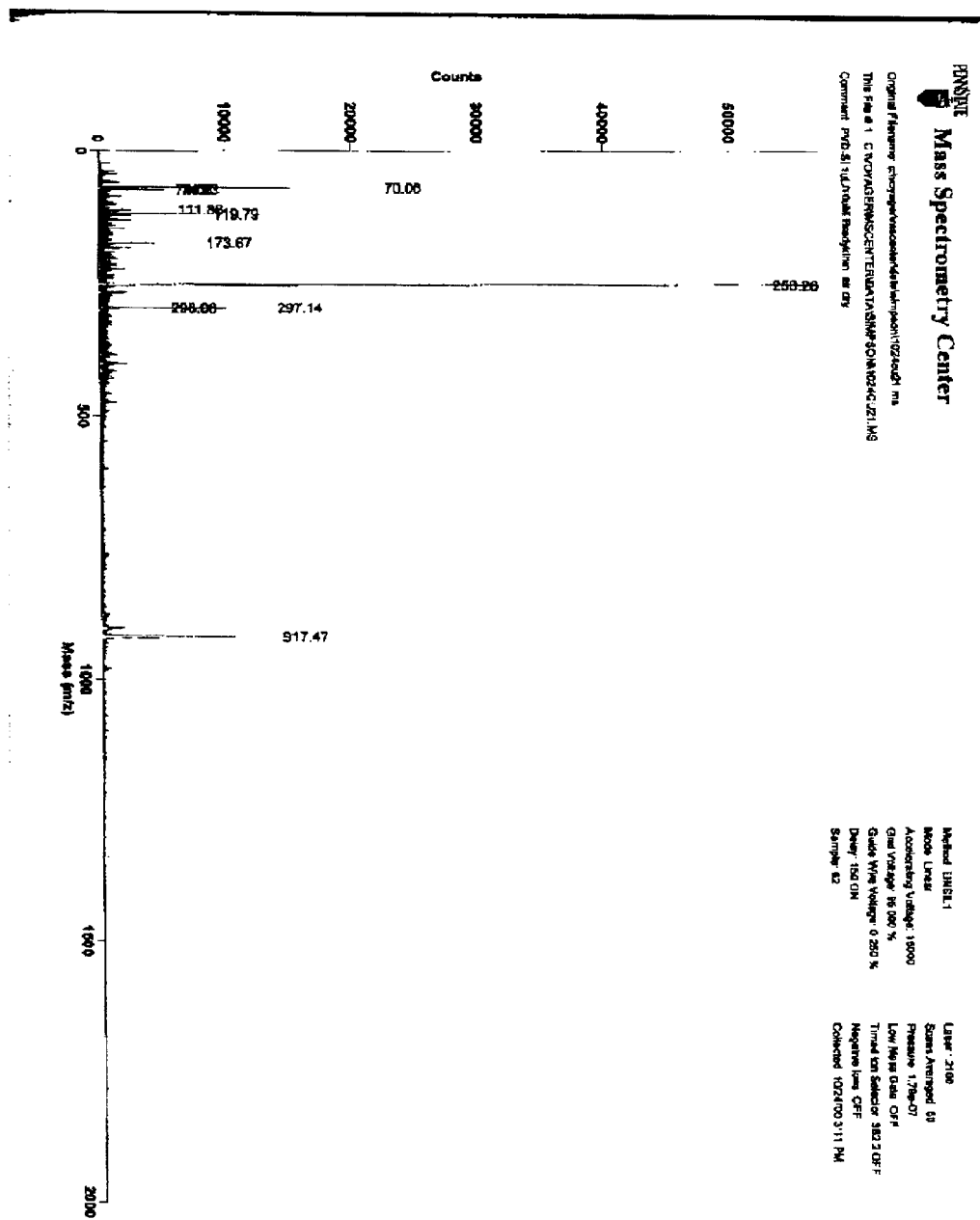
FIG. 3 is mass spectrum obtained using a medium morphology film; i.e., a film with the column structure as listed in Table 1. This particular example was deposited by e-gun PVD deposition. Low counts at the low mass range due to the lack of adsorbed hydrocarbons from the ambient are seen for this film.
Figure 4:
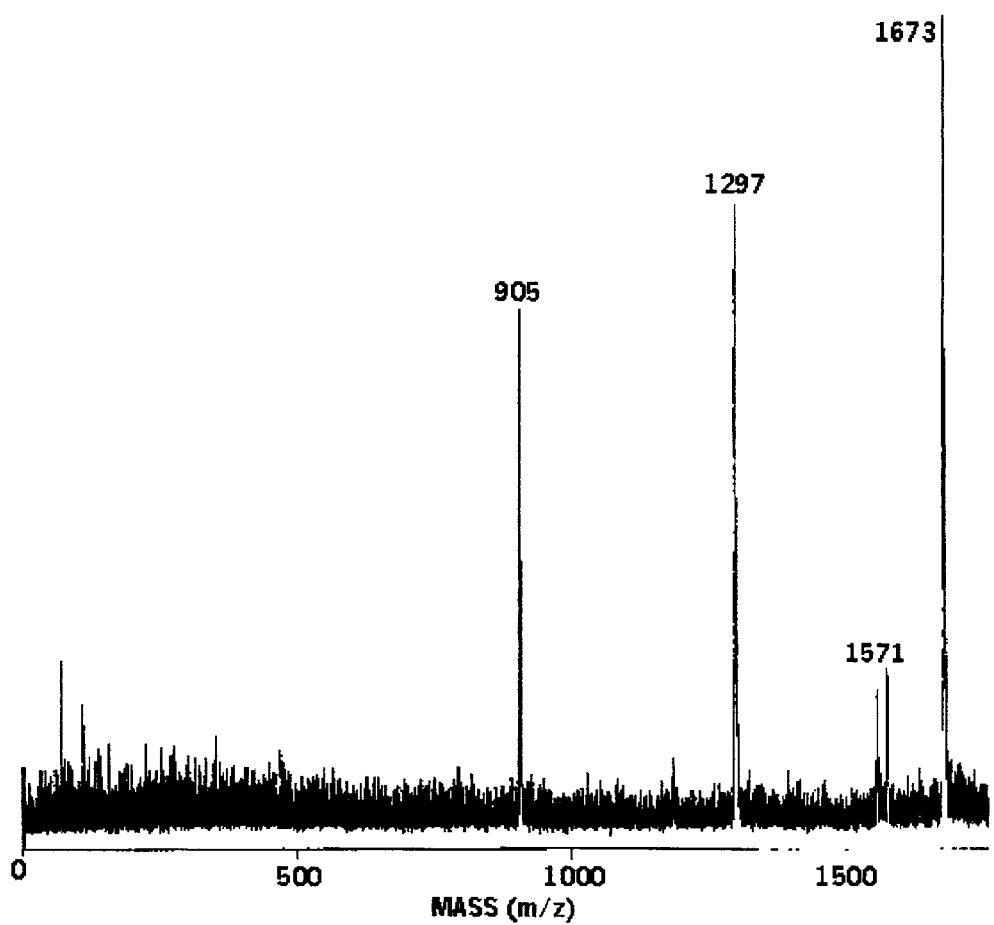
FIG. 4 is a mass spectrum obtained from a crystal silicon (wafer) surface. The continuous (no voids) films of Table 1 yield the same results; i.e., low analyte counts but also low noise from adsorbed ambients.

To evaluate these films glass substrates, coated with the silicon film substrates, were prepared with and without peptides (controls) or with and without cell structures (controls) and were attached to the standard MALDI sample plate simply using double-sided adhesive tape. Results for the nanostructured columnar/void network morphology substrates of Table 1 with and without peptides are shown in FIGS. 1 and 2. The results for this morphology show the clear high-count detection of the desired peptides with some low mass noise from adsorbed ambient species. Results for the column morphology substrates of Table 1 with peptides are shown in FIG. 3. The results show the clear detection of the desired peptides with further suppression of low mass noise due to less ambient adsorption for this type of film. This type of film is seen to sacrifice counts for noise suppression. Results for the continuous film (no voids) morphology substrates of Table 1 with peptides are shown in FIG. 4. These are specifically results for a silicon wafer but the results are identical for a continuous (no voids) morphology silicon thin film. These data show the (low count) detection of the desired peptides with enhanced suppression of low mass noise due to even less ambient adsorption for this type of film. This type of film is seen to be the other extreme from the columnar/void network morphology; i.e., a low analyte count yield is accepted for effective noise suppression due to very reduced ambient adsorption. Our approach using deposited thin-films offers improvements in reproducibility and manufacturing that make it very attractive for integration into high-throughput sample analysis systems (i.e., large-scale proteomics).

The demonstration of the deposited-dry etched columnar/void network film shows that these films can be grown with a variety of column diameters and thicknesses and a variety of void sizes between the columns. The voids in this film morphology according to the present invention are essentially continuous. They are formed in this specific demonstration by the simultaneous action of dry etching and deposition in a high-density plasma source. This etching/deposition is done at low temperatures and the films, therefore, can be grown on a variety of substrates including conducting metals, insulating dielectrics, and semiconductor materials. This variety of base layer materials can provide controllability over substrate-related issues (e.g., interference due to substrate, optical reflection/absorption, electrical conductance). The repetitive, connected pores and the columns can have their size and respective volume fractions adjusted. These adjustments can be made to vary chemical and physical behavior such as to enhance the trapping of specific size molecules and to vary optical reflectance. Chemical derivatization can be done to facilitate the trapping of specific molecules, cells, or cell products in specific regions of a substrate and the silicon columns of the columnar/void network act as excellent light energy absorbers.

There are several variables that can be controlled to tune this detection capabilities of these columnar/void network films. The first involves the film deposition parameters. By varying the plasma exposure conditions, the interplay of simultaneous plasma etching and plasma deposition can be adjusted systematically. In conventional porous silicon, the silicon is grown or deposited and then subsequently wet-etched. In the plasma-based approach of our demonstration of deposited columnar/void materials, the film is simultaneously plasma etched and plasma deposited in an interplay that is adjusted by varying plasma composition, pressure, power, and chamber configuration as well as temperature. Void density can be varied from zero (continuous film) up to about 90%. This allows the molecular, cell, or cell material trapping properties of the film to be adjusted at any film thickness. It allows the adjustment of the mixture percent of amorphous silicon and crystal silicon in the film thereby modifying optical properties, specifically tailoring the absorption of light from a source such as a laser source, giving laser desorption ionization. The $H_2$ content in columnar/void films can be controlled on silicon surfaces and in the columnar/void network silicon volume, for example, by changing deposition conditions. Therefore, the amount of hydrogen species production resulting from rapid heating due to laser or other light absorption can be tailored thereby contributing to the release of the analyte. Along with chemical treatments to stabilize, functionalize, or pattern the surface, oxidation or silicidation of the film can be used to impact film performance. Finally, the choice of substrate may also impact operation. These variable parameters provide a great deal of flexibility for films of a variety of thicknesses on a variety of substrates, and even allow for specialization of the film for particular molecule, cell, or cell material detections.

Our general approach of using low temperature deposited films and tailoring film morphology to the mass spectrometry application is very manufacturable and offers cost advantages. For example, our nanostructure columnar/void type thin film, demonstrated with high-density plasma deposition, is reproducibly made and inexpensive compared to wet electrochemically etched porous silicon. The ability to produce films on plastic offers a very low cost approach, enabling the possibility of one time use and disposal for clinical, industrial, and security applications. Also, the film is particularly good for light (e.g., laser) absorption because its optical absorption properties can be enhanced by the presence of the amorphous phase or nano-crystalline, enhanced absorption. Because of the absence of an organic matrix, this technique has the ability for ease of use with cells or cell material and detection of small mass particles and molecules, and higher resolution measurements. Because the films are grown under high vacuum, contamination of hydrocarbon and moisture due to air exposure can be prevented, if sealing procedures are used. Conversely, conventional porous silicon films are inherently contaminated because they are fabricated in air using wet chemicals and because some of the etchant/etching products will remain in the pores. Less contamination means less interference for analyte detection. Overall, the approach of this invention offers a low cost improvement to desorption mass spectroscopy.

This deposited thin film columnar/void network material offers several specific advantages to the electrochemically etched, random-pore silicon. For example, the deposited void/column film has a truly unique structure, which may be described as a nano-network with essentially continuous voids. Since the material is a thin film deposited at very low temperatures (<100° C.), the columnar/void network material has the ability to be grown on very inexpensive, disposable substrates such as plastic and glass which are ideal for throw-away clinical applications. The very fine, reproducible and well-ordered structure of the film and its large surface area immobilizes molecules very effectively and also offers the ability of molecular differentiation by transport through the void (pore) structure. The films have a porosity size and density that can be adjusted by the deposition parameters. The unique deposited columnar/void films of this invention are shown here to be able to detect organic proteins in the range of useful interest, demonstrated by the detection of proteins and peptides in the mass range of 0 to 6000 amu. Furthermore, the limits of molecular concentrations are theoretically comparable to that of MALDI. The present work is the first reported matrix-less MAIDI using a deposited silicon film.

The sample is applied to the film directly from, or integrated with, a chemical, physical, or electrical separation means, or combination thereof. The separation means is selected from the group consisting of: liquid chromatography, gas chromatography, deposited thin film chromatography, gel, capillary or micro-capillary electrophoresis, or blotting.

(A) Light (Laser) Desorption-Ionization: Application to Molecular Detection

The deposited continuous semiconductor films of Table 1 used for mass spectrometry were prepared in this demonstration using plasma enhanced chemical vapor deposition of silicon. The columnar semiconductor films of Table 1 used for mass spectrometry were prepared in this demonstration using physical vapor deposition of silicon. The nanostructured columnar/void network silicon films of Table 1 used to demonstrate deposited high surface area to volume ratio morphology were prepared by plasma enhanced chemical vapor deposition (PECVD). Specifically a high-density plasma approach using a Plasma Therm, electron cyclotron resonance (ECR) high-density plasma source was employed. This technique produces a nano-structured columnar silicon film at low substrate temperatures (100° C.). Films with these three types of morphology were deposited on various substrates. For example, polyethylene terephthalate (PET) and glass (Coming 1737) substrates were coated with between 500 and 10,000 angstroms of the deposited columnar/void network silicon film. In the case of this morphology, depositions were controlled to give a range of porosities (void densities) with and without a silicon nitride base layer. Post deposition surface modifications to the films were explored including: growth of a thin silicon dioxide layer, silanization with 3-aminopropyltriethoxysilane (from Sigma) and light mediated surface functionalizations with 1-hexyne, 5-hexyn-1-ol, 1-decyne, and 9-decen-1-ol (all at least 97% pure). Other substrates such as gold, glass, thermal silicon oxide and silicon wafers were also used for comparison.

The proteins, peptides and ammonium citrate used to demonstrate matrix-less mass spectroscopy with the three film morphologies of Table 1 were obtained from Sigma and the trypsin was frozen, sequencing grade from Promega. Organic solvents such as methanol, acetonitrile, and DMSO were added in some cases for signal comparison (all HPLC grade from EM Science). In the case of ubiquitin, test solutions for the mass desorption study were made using HPLC purified compounds and deionized water or ammonium bicarbonate (0.1 M, pH 7.8) for the tryptic digest reactions of ubiquitin. The matrix-free preparation of samples on our various material surfaces was done by allowing a 0.5–1 μL drop of the sample to air-dry on the surface or by our unique approach of applying the analyte solution and then systematically removing it, leaving behind absorbed species. This latter approach uses the adsorbing characteristics of films with voids. On-column desalting was performed on Zip Tip (Millipore Co.) $C_{18}$ resin pipette tips.

All samples were analyzed using a Perseptive Biosystems (Framingham, Mass.) Voyager-DE STR mass spectrometer using 337 nm light from a nitrogen laser. Substrates were attached to the face of the conventional MALDI target using double-sided tape. Analyses were performed in linear mode with instrument parameters identical to normal MALDI operation except no low-mass cut-off was employed.

Figure 5:
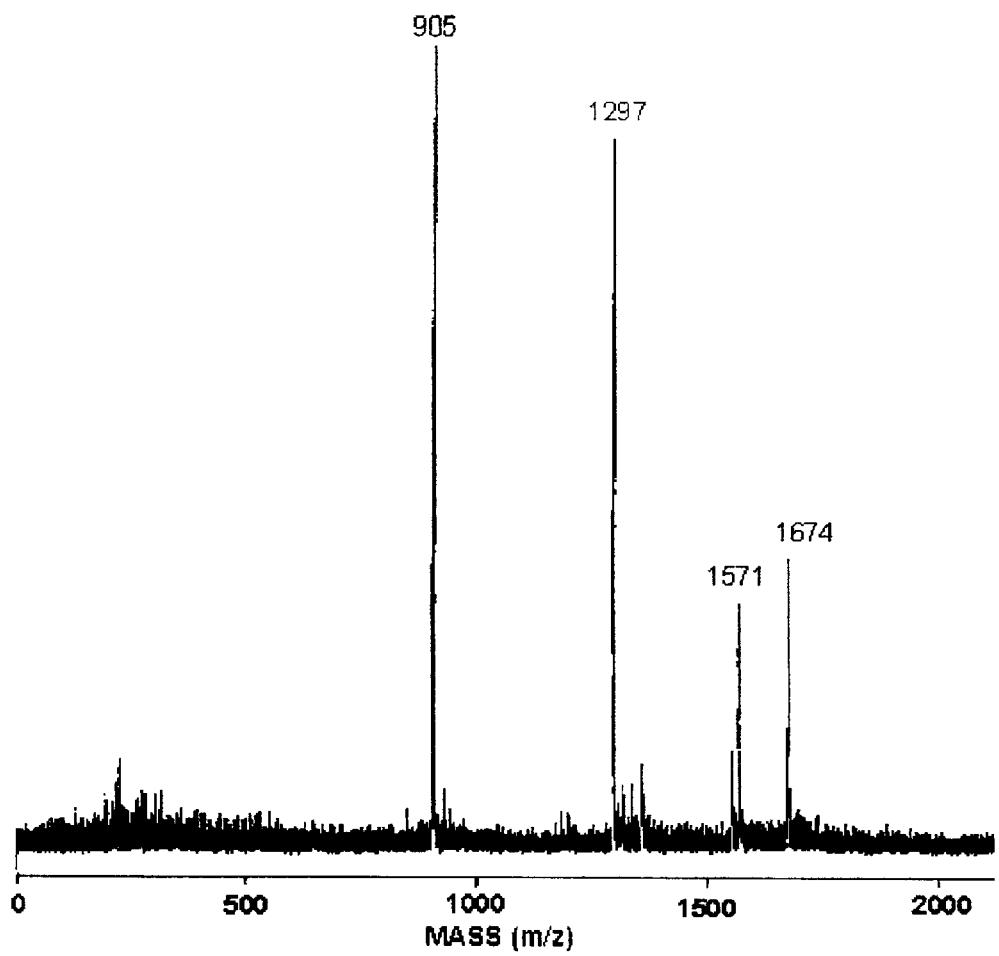
FIG. 5 is a mass spectrum obtained from a silicon dioxide coated silicon wafer.
Figure 6:
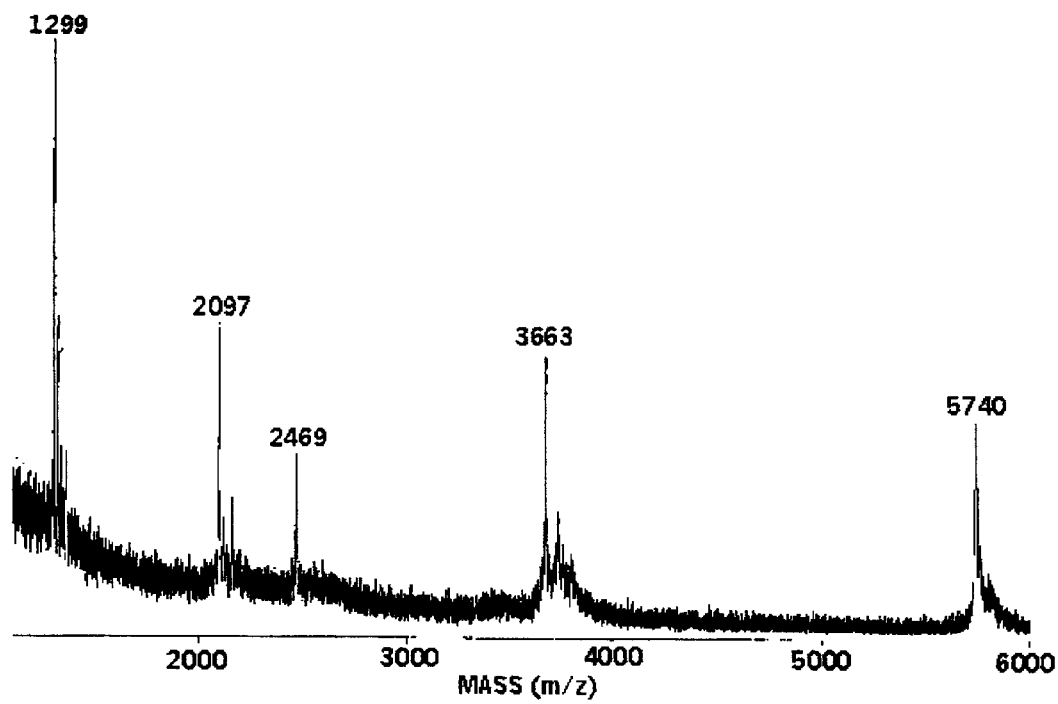
FIG. 6 is a higher mass spectrum obtained from samples on silicon dioxide coated silicon wafer.
Figure 7:
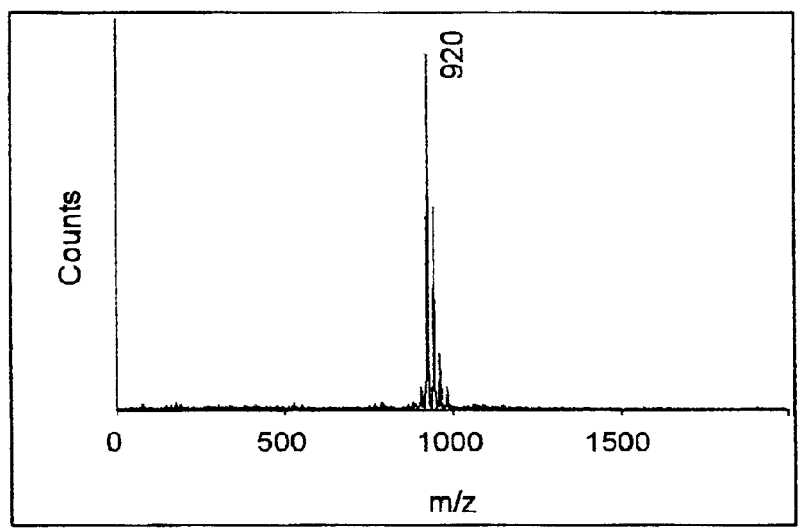
FIG. 7 is a mass spectrum resulting from application of and removal of a 1 $\mu$L drop of a 1 $\mu$M des-pro$^3$, (ala$^{2,6}$)-bradykinin (m/z 920) solution on a columnar/void network silicon thin film substrate.
Figure 8:
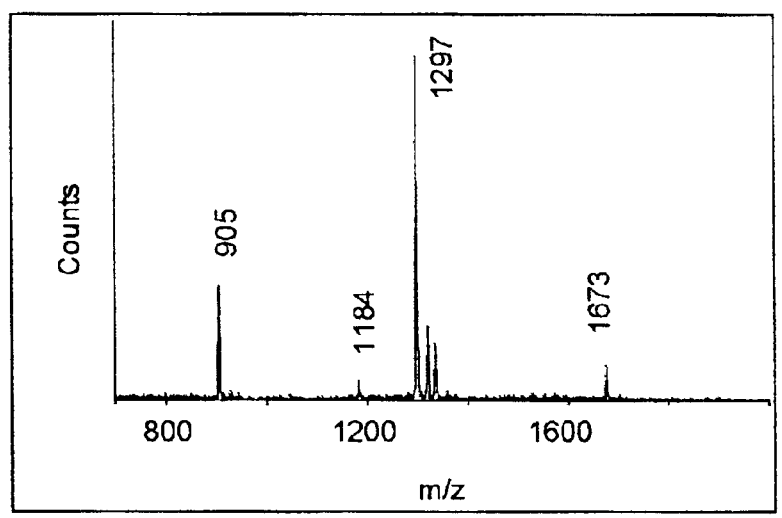
FIG. 8 is a mass spectrum of a mixture of peptides, all in the pico-Mole range, including des-arg1-bradykinin (m/z 905), angiotensin I (m/z 1297), and neurotensin (m/z 1673) obtained using a glass substrate coated with columnar/void network silicon thin film.
Figure 9:
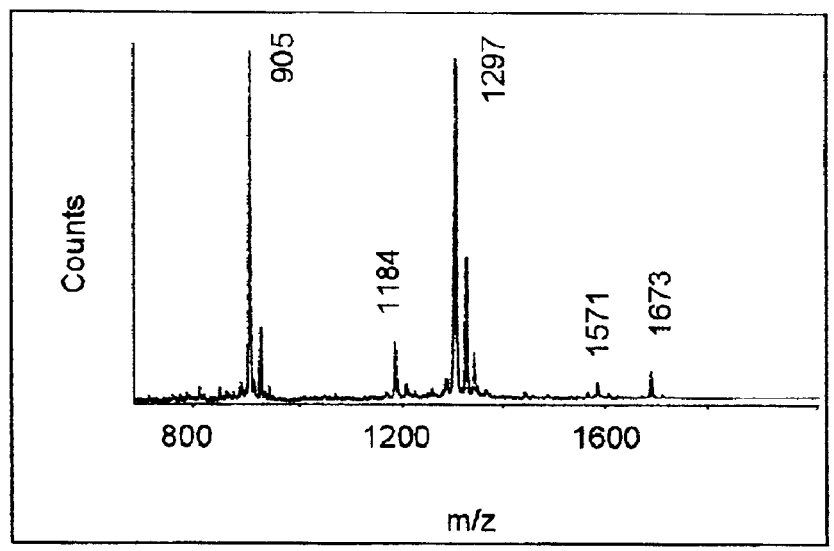
FIG. 9 is a mass spectrum of a mixture of peptides, all in the pico-Mole range, including des-arg1-bradykinin (m/z 905), (m/z 1184), angiotensin I (m/z 1297), glu1-fibrinopeptide B (m/z 1571), and neurotensin (m/z 1673) on a plastic substrate coated with columnar/void network silicon thin film.
Figure 10:
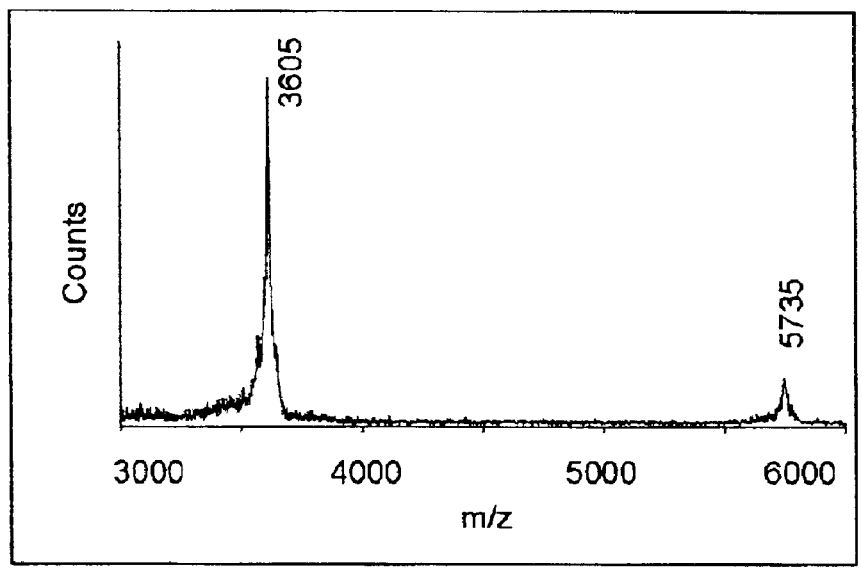
FIG. 10 is a mass spectrum obtained from a 1 $\mu$L drop of a 5 $\mu$M solution of thyrocalcitonin (m/z 3605), insulin (m/z 5735), and other smaller peptides on a columnar/void network silicon thin film substrate.

The results not only show the usefulness of the deposited thin-film nano-structured columnar/void silicon for laser desorption but also give insight into some of the mechanisms governing desorption and ionization on these films. The results also show that continuous (void free) films of Table 1 can be useful when noise from adsorbed ambients must be suppressed even at the expense of detection counts for the analyte. The results further show that the columnar films of Table 1 can be useful in suppressing noise from adsorbed ambients without the extreme compromise of the analyte counts seen in the continuous film morphology. FIGS. 1–13 demonstrate the performance of our films as a light (laser) desorption substrate. FIG. 3 shows results from a column morphology film and FIG. 4 typifies results from a continuous (void free) film. FIGS. 5 and 6 show the impact of using anti-reflection (AR) coatings using films of FIG. 4 morphology. FIGS. 7–13 are for the nanostructured columnar/void network morphology films. FIG. 7 shows the detection of des-pro$^3$,(ala$^{2,6}$)-bradykinin at m/z 920 with surrounding peaks (at m/z 943 and 959) corresponding to sodium and potassium attachment. This plot demonstrates the utility of our deposited columnar/void network film material in yielding high analyte counts and clear detection of the peptide. FIGS. 8 and 9 give spectra of a mixture of peptides on a columnar/void network film coated on glass (FIG. 8) and plastic (FIG. 9). FIG. 10 provides the spectra of proteins with masses ranging from 3000–6000 Daltons, in which insulin (m/z 5735) is detected. Although the lower mass range of the spectrum in FIG. 10 is not given for simplicity, it is important to note that the larger molecules were still able to be detected when competing for energy and charge in the presence of smaller peptides such as bradykinin and angiotensin, present in the mixture adsorbed onto the columnar/void network morphology film. The limit of detection for bradykinin was 50 femto-moles.

Figure 11:
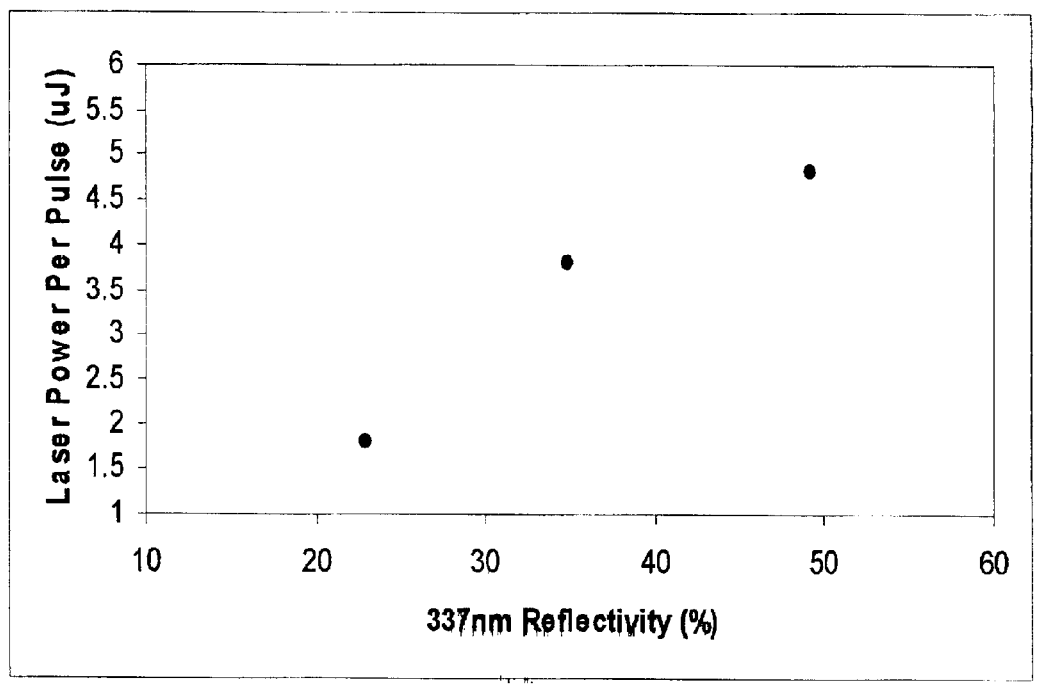
FIG. 11 is a plot showing the minimum laser power per pulse necessary to obtain a mass signal for des-pro$^3$, [ala$^{2,6}$]-bradykinin versus columnar/void network silicon thin film reflectivity.

Although the mechanisms for ionization are quite complex, energy transfer from the incident laser to the sample molecules is a very important process in our technique as well as in MALDI. No observable peptide signal was obtained if the sample molecules were placed on a metal surface, where the laser light reflects efficiently, or on a glass surface, where the laser light is poorly absorbed. The molecules did, however, desorb and ionize on a silicon wafer with or without an antireflection layer (silicon dioxide) (FIGS. 4, 5 and 6), on deposited continuous (no voids) silicon films (same as FIG. 4), and on the columnar film morphology silicon. The analyte counts are the lowest on wafer or continuous film silicon, higher on column morphology silicon films, and highest on the nanostructured columnar/void network material. For the same ambient exposure the noise from adsorbed ambients is the worst for the columnar/void material, less severe for the column morphology material, and least for the continuous film material. The superior analyte-counts results obtained when using the columnar/void network material indicate that a critical element of the laser desorption process is the coupling of the laser light into the substrate. The UV reflectance of the deposited nano-structured columnar/void network silicon films, the lowest reflectance of the three types of film morphologies, can be tailored by adjusting the deposition parameters. With our high-density plasma deposition process, highly repeatable normal incidence UV reflectance between 10–50% at 337 nm can be obtained by varying the process parameters. For comparison, the UV reflectance of a silicon wafer with or without the extra step of a silicon dioxide anti-reflection coating ranges between 40–70% at 337 nm. FIG. 11 shows the relationship between the minimum laser power necessary to detect bradykinin and the 337 nm reflectivity of the deposited columnar/void network silicon films. The low reflectance possible with the films (seen in FIG. 11) is advantageous, because lower laser power reduces kinetic energy transfer and may improve high-resolution spectra.

Figure 12:
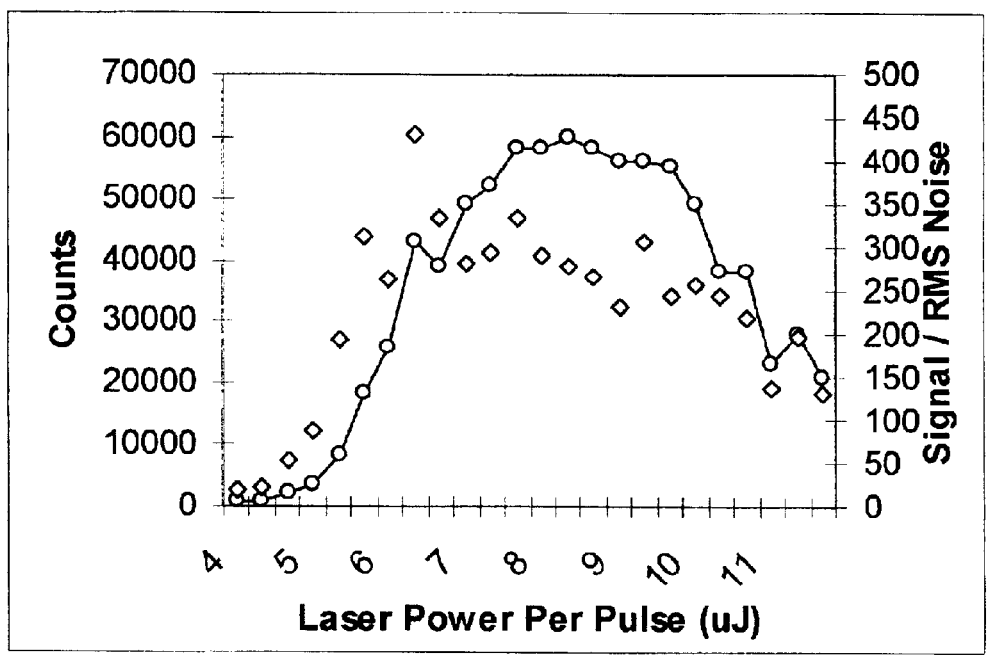
FIG. 12 is a plot showing detection characteristics of des-pro$^3$, [ala$^{2,6}$]-bradykinin versus laser pulse power. The circle (○) and the diamond (◇) correspond to relative des-pro$^3$, [ala$^{2,6}$]-bradykinin counts and RMS signal to noise, respectively. The substrate is the columnar/void network material.

To observe the effects of laser power with our deposited nanostructured columnar/void network Si films, the mass analysis using semiconductor films (MASF) detection of bradykinin was characterized using various laser powers. FIG. 12 shows the trends in bradykinin counts and signal to noise ratios versus laser power. At low laser energies the bradykinin signal increases with increasing power. However, as the laser power continues to increase, the molecules begin to break down before detection, lowering the counts and signal to noise ratio. FIG. 7 gives the spectrum corresponding to the highest signal to noise ratio point on this plot. The data in FIG. 12 demonstrate a laser power range suitable for sample detection is in this case, between 6–10 µJ per pulse with a spot size of approximately 200 µm.

Figure 13:
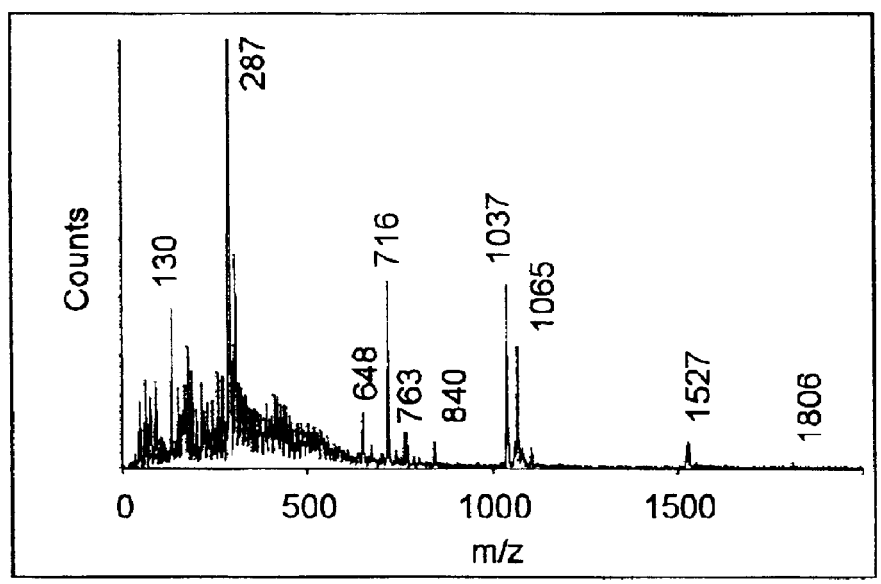
FIG. 13 is a mass spectrum obtained from a column desalted tryptic digest of ubiquitin (1 $\mu$M pre-digest) with the addition of ammonium citrate (250 $\mu$M ammonium citrate), (1:1 mixture). The substrate is the columnar/void network material.

Solution tryptic digests of ubiquitin were conducted to determine the suitability of these columnar/void network films for peptide mass mapping. By eliminating matrix compound contamination, our mass analysis using semiconductor films (MASF) approach allows useful low mass data to be collected for small peptides and molecules. The addition of ammonium citrate to post digestion reaction mixtures dramatically improved the ability to detect peptide fragments. FIG. 13 demonstrates nine peaks corresponding to predicted ubiquitin tryptic digest fragments or common products of incomplete digestion.

Light and chemically mediated molecular attachment to the surface was performed on the columnar/void network morphology material used for FIG. 7 to study the effects of mediation and of hydrophobicity and hydrophilicity on signal acquisition. To achieve the various modified surfaces, six and ten carbon chain molecules were attached with both hydrogen and alcohol terminated ends. It was observed that all such modified films required an increased laser power for detection but displayed no change in the reflectivity. This indicates that the extra molecular layer or layers between the analyte and nano-structured surface reduces the energy transfer efficiency, but these data establish that surface treatments, can be used effectively to functionalize surfaces in MASF; i.e., desorption and ionization are still enabled after such treatments.

We have also explored adding organic solvents to the molecular samples before their application to the deposited columnar/void network morphology silicon surface. Primarily the samples were prepared with HPLC purified molecules dissolved in deionized water; however, the effects of various additional solvents were also examined. In general, it was found that these additional solvents advantageously or disadvantageously affected the way drops dried and therefore modified the state of the analyte on the surface. A specific example of these effects can be found in samples that contained more than 25% acetonitrile. Drops from such a sample have low surface tension and quickly spread over a large surface area, reducing signal intensity. Some solvents such as DMSO have extremely low vapor pressures and will not dry within a reasonable amount of time at room temperature conditions. Purity of the organic solvents also must be considered because of the sensitivity of this technique to low-mass contaminants that can be included in the signal.

The deposited columnar/void network morphology films are extremely effective in adsorbing and fixing atomic and molecular species, including atmospheric species. Over a period of days after deposition, low-mass noise begins to appear along with the desired spectrum obtained using the films. Such "molecular and atomic flypaper" can be used for environmental monitoring applications. Alternatively, such contamination can be avoided with careful storage and handling techniques. Defining the surface state of the film in a vacuum, as is done by using vacuum deposited films, and not in an etching bath yields controllability that is very important for clinical and drug development applications where contamination issues can be most critical.

Figure 14A:
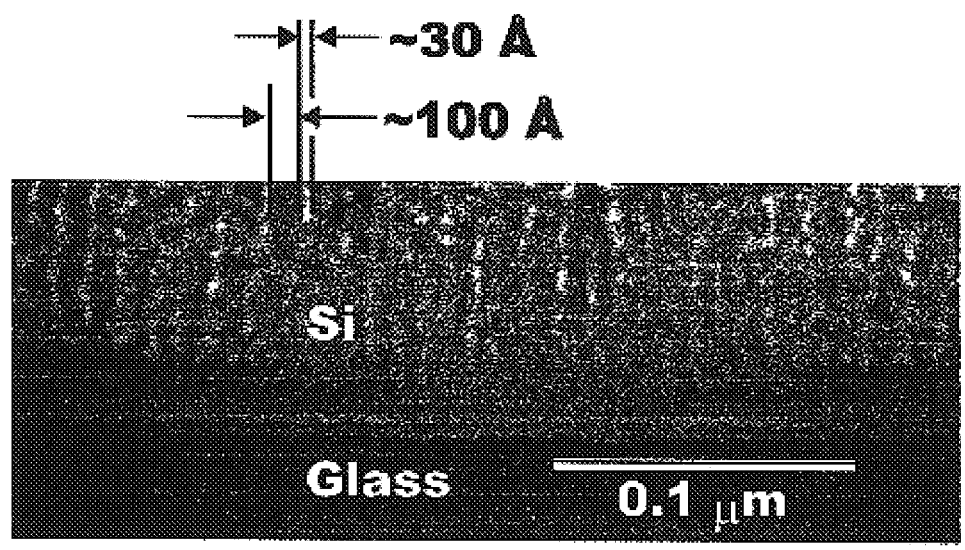
FIG. 14a is a cross-sectional TEM of a nano-structured columnar/void network film of Table 1.
Figure 14B:
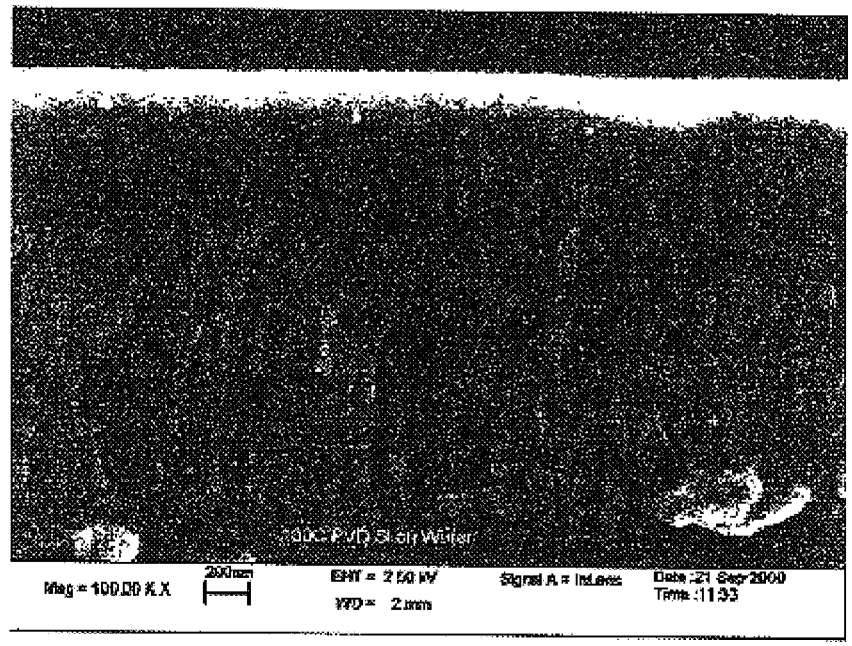
FIG. 14b is a cross-sectional SEM of column structure film of Table 1. This particular example of the column morphology was deposited by e-gun PVD deposition. The data of FIG. 3 are obtained using the medium morphology film substrate of Table 1 morphology.

In sum, a non-matrix laser desorption ionization technique for molecule and molecule fragment analysis has been developed based on deposited semiconductor thin films. The morphology of these films varied from continuous (void free) to column structure morphology (FIG. 14b) and to nanostructured columnar/void network morphology (FIG. 14a). The vacuum preparation of these deposited films avoids contamination issues. In particular, it avoids the contamination issues found for porous silicon prepared by etching and exposure to wet solutions and electrodes. These films, which can be deposited on flat or even curved metal foils, plastics or glass, can be sealed after fabrication and only exposed at the time of sample preparation or they can be used as "molecular flypaper" for environmental monitoring. The nano-structured deposited films enable molecular detection with no mass noise coming from the presence of a matrix material; i.e., the matrix material of MALDI is avoided. If any low mass noise coming from ambient exposure must be suppressed, the column morphology film can be used in place of the nanostructured columnar/void network material. This results in a trade-off: less ambient noise but lower analyte counts for the same laser intensity. If the possibility of any low mass noise from ambients is to be suppressed further, then continuous films may be used but at the further loss of analyte counts for the same laser intensity. In addition, surface functionalization can be used to extend the mass range, for example, for these films. These results, comments, and additional observations are summarized in Table II below.

TABLE II

Advantages and Disadvantages of Various Substrates

| Substrate | Advantages | Disadvantages | Cost | General Comments* |
|---|---|---|---|---|
| Si-wafer | Low hydrocarbon noise<br>Reproducible substrate<br>High chemical stability | Drop drying problematic<br>Low adsorption of analyte | High | Low surface area<br>High reflectivity |

TABLE II-continued

Advantages and Disadvantages of Various Substrates

| Substrate | Advantages | Disadvantages | Cost | General Comments* |
|---|---|---|---|---|
| Porous Si Material (DIOS material of Prior Art) | Reproducible drop drying possible with our drying technique. High adsorption of analyte | High hydrocarbon noise. Not easy to reproducibly make this wet etched material substrate. Electro-chemical wet chemistry process needed for manufacture. Manufacturability is problematic. Impurities trapped in material in fabrication process. Low chemical stability. Degrades with time | Could be very high due to preparation approach (i.e., electro-chemical etching) if manufacturable | High surface area. Low reflectivity. High steric interaction |
| Deposited Continuous (void free) Films of this Invention | Low hydrocarbon noise. Reproducible deposited thin film substrate. Low process temperature. Chemically stable | Drop drying problematic. Relatively low adsorption of analyte | Low and compatible with low cost substrates (even plastic or glass can be used) | Low surface area. Medium reflectivity |
| Deposited Column Structure Films of this Invention | Low hydrocarbon noise. Reproducible deposited thin film substrate. Low process temperature. Chemically stable | Drop drying somewhat problematic | Low and compatible with low cost substrates (even plastic or glass can be used) | Relatively low surface area compared to Columnar/void Network Material. Medium reflectivity |
| Deposited Nanostructured Columnar/Void Network Films of this Invention | At 6 mTorr deposition in ECR, low hydrocarbon noise. Reproducible deposited thin film substrate. Reproducible drop drying. High adsorption of analyte. Low process temperature | At 8 & 10 mTorr deposition in ECR, high hydrocarbon noise. Adsorbs ambient species readily; requires protection from ambient unless used for ambient monitoring | Low and compatible with low cost substrates (even plastic or glass can be used) | Very high surface area. Low reflectivity. High steric interaction |

Figure 15:
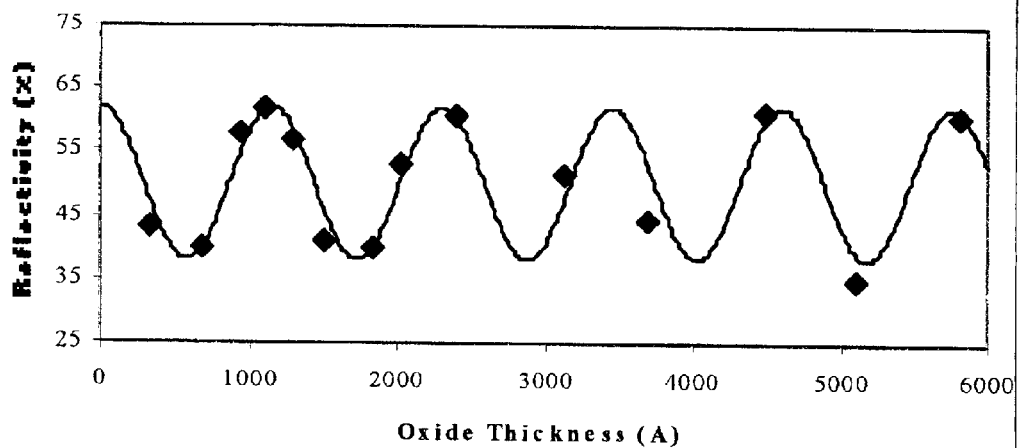
FIG. 15 is a graph of relative 337 nm light reflectivity versus oxide coating thickness.

*High optical reflectance is disadvantageous but can be overcome by increasing laser power. High surface area is advantageous for the adsorption of analyte molecules and species from drops and for drop drying but can be disadvantageous in situations where inadvertent adsorption of impurities occurs. Steric interaction may improve energy transfer to large molecules, but also may hinder their release In light (laser) desorption using the matrix-less approach, rapid thermal heating of non-matrix substrates is what releases the molecules from the surface. The technique, therefore, is dependent on the effective optical coupling of the laser energy. Silicon absorbs UV radiation very well, but it also reflects much of the incident light due to the abrupt change in the index of refraction present if light goes directly from air (or vacuum) into the silicon. Reflection losses can be overcome, thereby increasing the effectiveness or matrix-less line of flight mass spectroscopy, by better optical impedance-matching at the silicon surface. This better optical impedance matching can be achieved in one of two ways. One is by gradually changing the index of refraction at the silicon surface. This is demonstrated by the conventional porous silicon materials produced by etching and by our columnar/void network morphology silicon films described herein. Another method of impedance matching is to provide an anti-reflection (AR) coating on top of silicon, which may be a wafer, a planar deposited Si film, a porous Si material, or our deposited columnar/void network Si material. Obviously other semiconductors may also be used in place of the Si. FIG. 15 shows the results of our reflectivity study done with various thicknesses of $SiO_2$ on (planar, smooth) crystal silicon at a light wavelength of 337 nm, the same used in UV MALDI. These data are for light normally impinging on the surface. Since there is no columnar/void network material present, optical coupling via the $SiO_2$ functioning as an anti-reflective coating is the only optical impedance method possible. The points are experimentally obtained values, while the solid line is a first order prediction of how the reflectivity should vary based on optical interference, with vertical adjustments made to fit the observed relative reflectivity.

Figure 16:
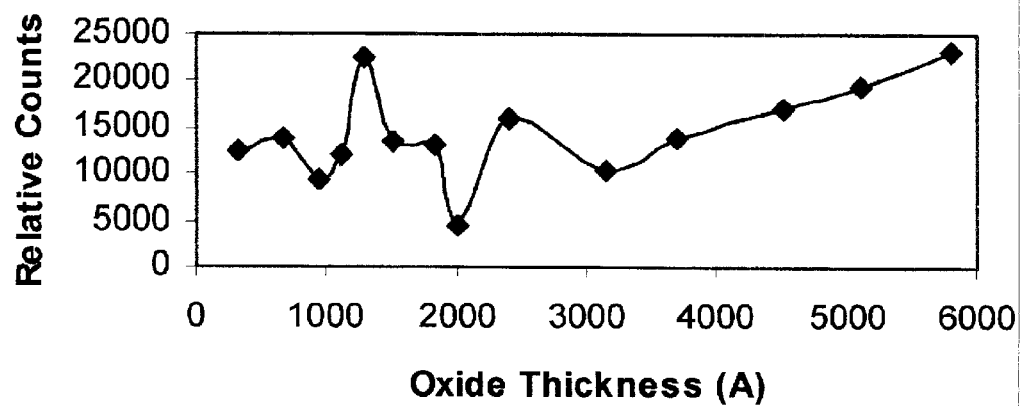
FIG. 16 is a plot of average sample counts versus oxide thickness.

To confirm that optical coupling plays an important role in laser desorption/ionization, the planar Si wafer samples used to obtain reflectivity measurements were used as substrates for non-matrix molecular detection. A plot of average sample counts versus oxide thickness is given in FIG. 16. This plot clearly indicates a periodic signal dependence on oxide thickness similar to the reflectivity study. It is difficult to directly compare the reflectivity and spectroscopy results because of the difficulty to obtain perfectly consistent mass spectra and the non-perpendicular incident laser beam. The laser used on the MALDI system is approximately at a 35° angle to the normal and, therefore, will not show interference effects after an oxide thickness of a several photon wavelengths and will shift the peaks and valleys of the reflectance plot.

Other results that agree with this model are as follows. No signal has been found for molecules on metallic substrates because of their very high reflectance of UV light. No signal was received from samples on a glass ($SiO_2$) substrate approximately 0.7 mm thick with amorphous silicon on the back surface. This eliminates direct interaction of the laser with the molecules and also suggests that the large thickness of glass prevented the thermal energy generated in the a-Si from reaching the molecules on the surface.

While the data just presented shows that the use of deposited anti-reflection coatings can be used to enhance matrix-less laser desorption mass spectroscopy (and probably conventional MALDI too), these data do also show that the use of AR coating requires fairly careful control of the coating thickness.

Figure 17:
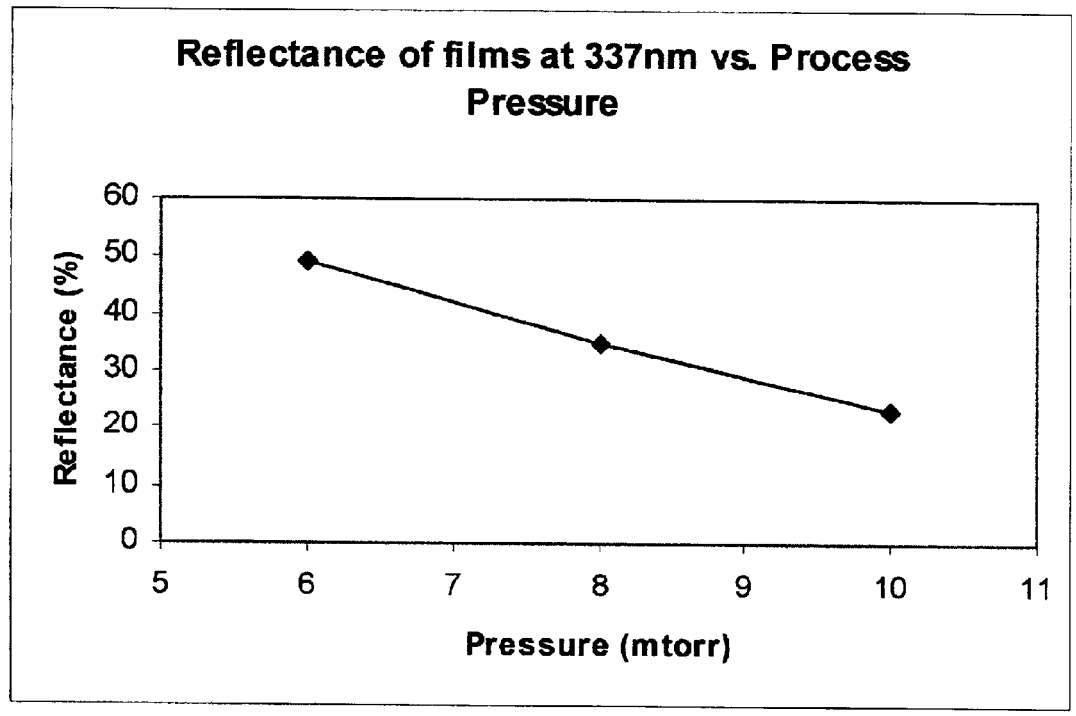
FIG. 17 is a graph of reflectance of columnar/void network films at 337 nm vs. process pressure.

The use of our nanostructured columnar/void network material for optical impedance matching very effectively couples light to cause laser desorption, as shown earlier, and has the distinct advantage of not requiring thickness control. In fact, the effectiveness of our films in the optical coupling function is varied by changing the columnar/void network size features. That is, by adjusting the in-situ and post-deposition processing of the film, its properties can be tailored regarding the coupling of optical energy. For example as shown in FIG. 17, we can adjust how much UV laser light (337 nm) is reflected by the film. In this case, we adjust the process pressure to change the columnar/void features. This changes how well the UV light reflects off of and is absorbed into the film. The process pressure directly correlates to the percent reflectance of the film.

In summary, each method of optical impedance matching (i.e., the use of columnar/void network material or the use of AR coatings) offers its own unique features. The void/column film offers very strong optical coupling (low reflectance) without the need for film thickness control. The anti-reflection layer ($SiO_2$, $Si_3N_4$, transparent conducting oxides (TCO) coated silicon has the ability to couple almost all of the laser energy into the substrate thereby very effectively thermally exciting the molecules to be detected. This allows for the possibility of extremely sensitive detection of molecules. This AR coating approach allows planar (i.e. non-porous) silicon (and other semiconductors) to be used. These may be deposited or conventional etched porous films. Also, since TCO materials can be used for the AR coating, this approach provides a solution if surface charge buildup becomes an issue. The drawback of the AR coating approach is the need for AR film thickness control.

We have used both of these techniques for enhanced optical coupling (optical impedance matching), as our data shows, to detect molecules in the range of 0 to 6000 amu and both have the potential to measure much higher molecular weights, theoretically comparable to that of MALDI. Overall, both of these optical coupling techniques are unique and offer a very practical and easy to implement method for matrix-free, efficient biological mass spectroscopy.

(B) Light (Laser) Desorption-Ionization: Application to Viral, Bacterial or Whole Cell Mass Spectrum Finger Printing MASF can be used as to determine the identity of intact viruses, prokaryotic and eukaryotic cells by a characteristic mass spectrum fingerprint of the organism. In this technique, whole organisms or cells are brought into contact with the nanostructured columnar/void silicon thin film and analyzed by laser desorption and ionization, time of flight mass spectrometry.

Figure 18A:
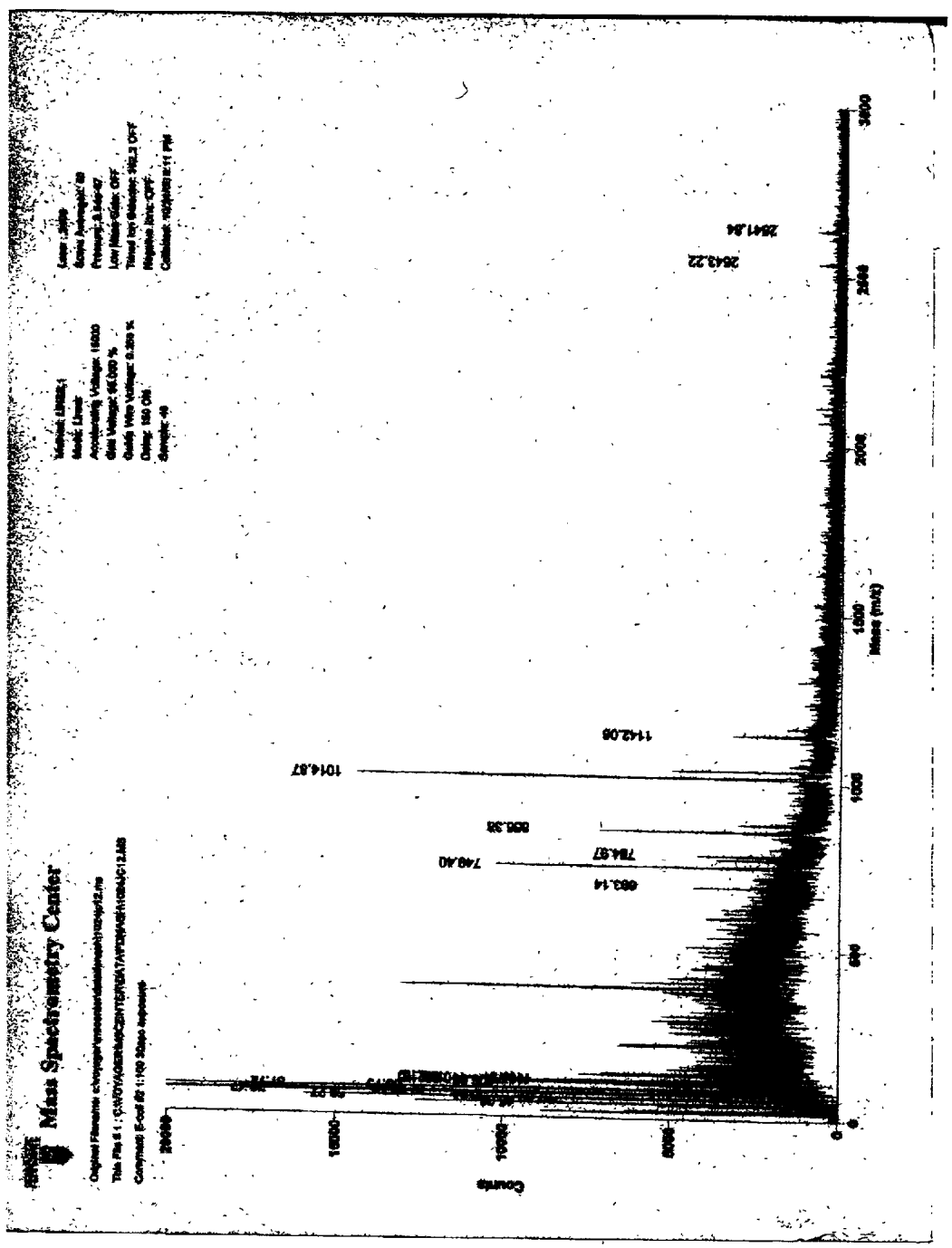
FIG. 18a is a MASF spectra of cloning grade *E.coli* culture #1.
Figure 18B:
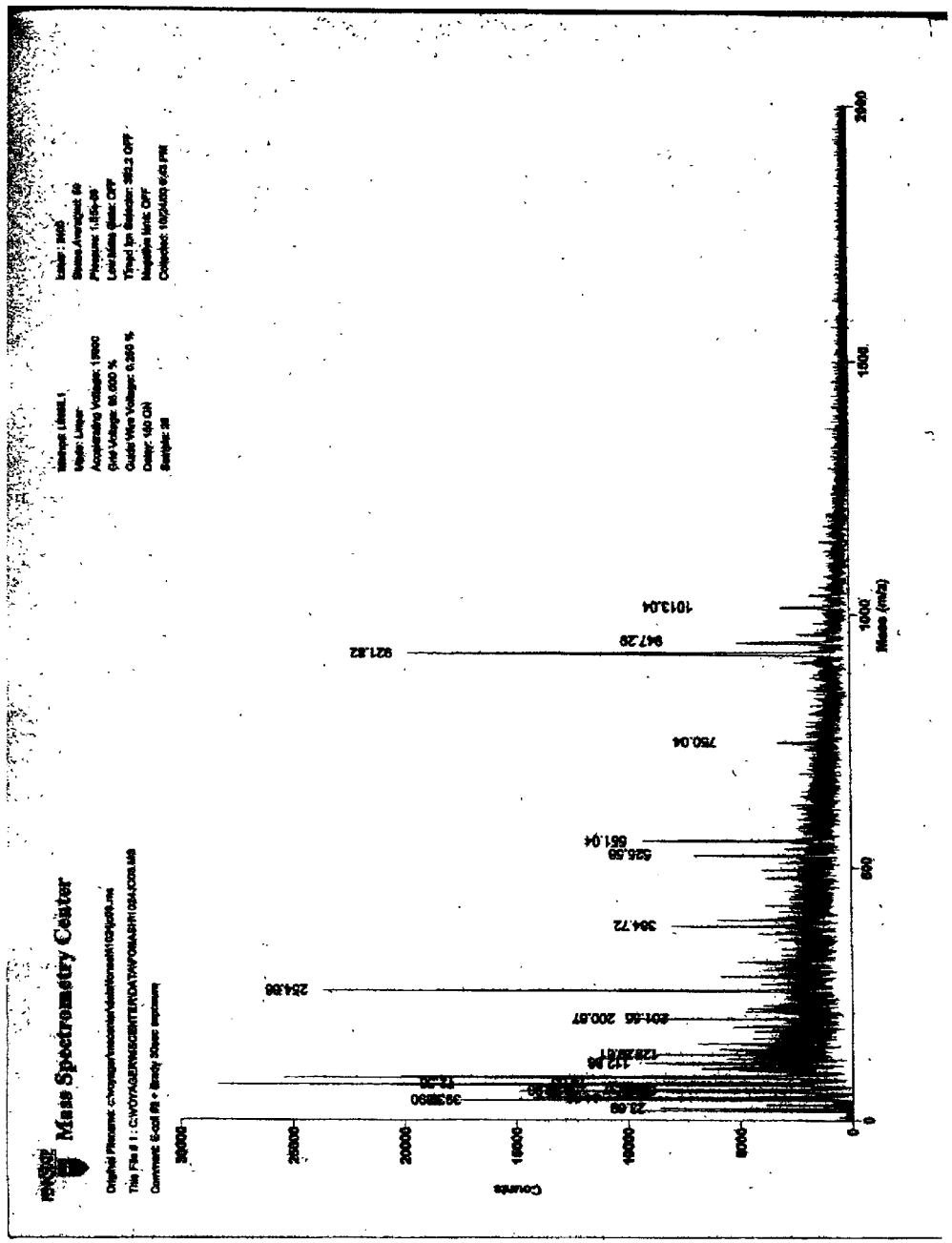
FIG. 18b is a MASF spectra of cloning grade *E.coli* culture #2 including one pico-Mole of des-pro$^3$,(ala$^{2,6}$)-Bradykinin internal standard (m/z 921).

Demonstrated in this application are the following: two separate cloning grade E.coli cultures are analyzed by MASF and shown to provide consistent and reproducible mass spectra. The cultures were grown overnight in Lauria Broth at 37 degrees Celsius. The E.coli bacteria were isolated and washed by repeated centrifugation and dilution steps. After isolation and washing the whole cell bacteria samples were exposed to the continuous columnar/void silicon thin film for 30 seconds. The MASF spectra of an E.coli can be seen in FIG. 18a. A comparative sample from the second culture, including one pico-Mole of des-pro$^3$, (ala$^{2,6}$)-Bradykinin internal standard (m/z 921), is seen in FIG. 18b.

Figure 19A:
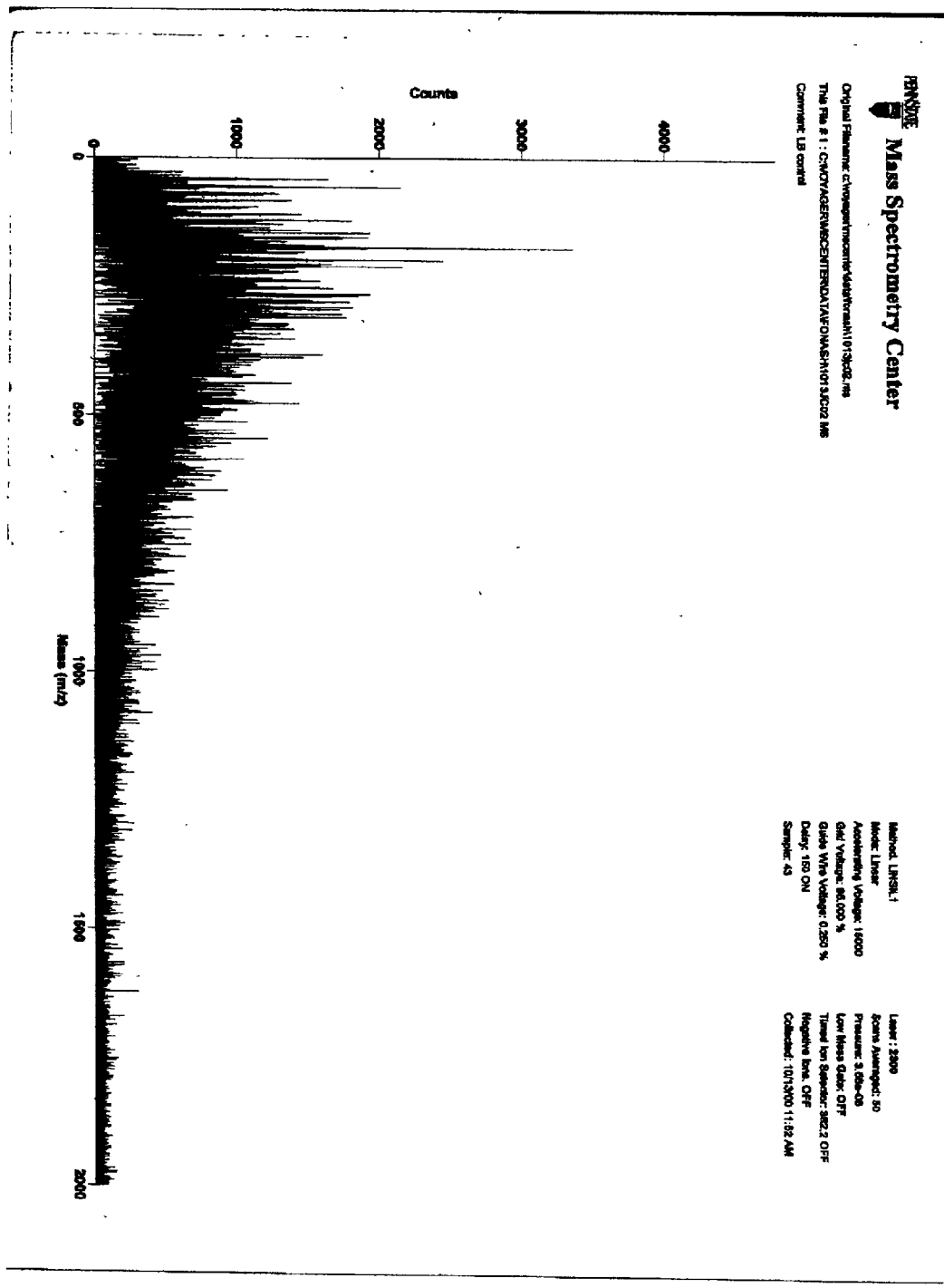
FIG. 19a is a MASF spectra of control LB bacterial culture media.
Figure 19B:
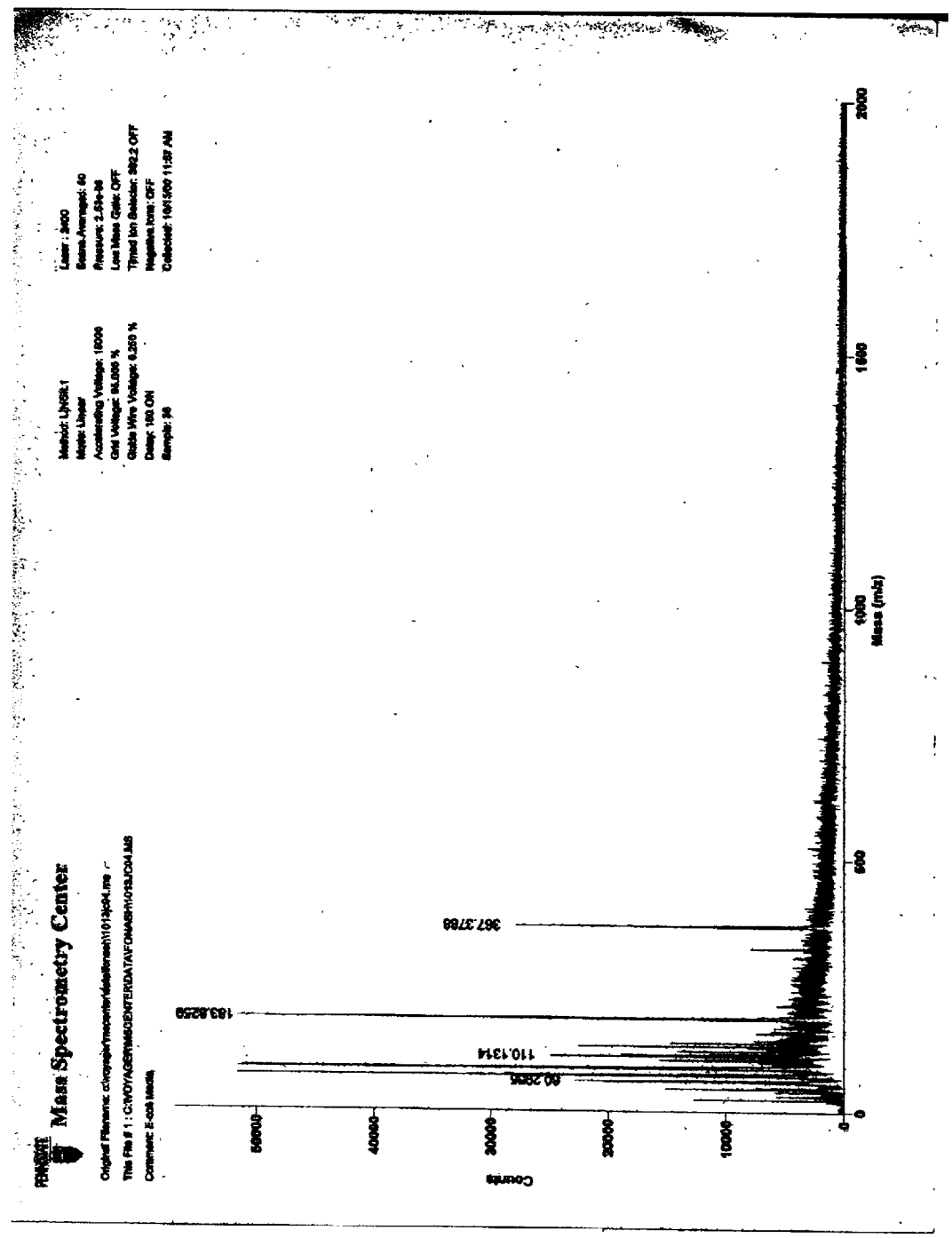
FIG. 19b is a MASF spectra of *E.coli* inoculated LB bacterial culture media.

MASF can also be used to detect, from bacterial culture, common soluble metabolic byproducts from the culture media. FIGS. 19a and 19b show the MASF spectra from a non-inoculated control lauria broth and an inoculated sample respectively. Two clear peaks can be seen in the broth isolated from the inoculated sample. The lauria broth samples were taken after the initial centrifugation step to remove non-adherent bacteria and particulate matter.

(3) Cell Attachment and Growth Support

The continuous columnar/void silicon network films provide an excellent surface for prokaryotic and eukaryotic cell attachment, differentiation and proliferation. Both the topology and chemical make up of the surface promote cell attachment. Surface patterning, chemical modification, protein absorption and the application of electric and magnetic fields can be used to tailor the surface and local environment for cell attachment, differentiation and proliferation.

Specifically, continuous columnar/void silicon network films have been used as the substrate in cell attachment and directional growth studies. Experiments have been conducted using electro-active Nerve Growth Factor treated PC 12 cells. PC 12 cells were plated on collagen micropatterned continuous columnar/void silicon network films and exposed to pulsed DC electric field. The collagen micropatterning was accomplished with a microfabricated PDMS stamp which was used to print 37 micrometer collagen lines. 2 mV DC electric pulses were applied through the use of an agarose salt bridge, with the field aligned parallel to the collagen lines. The cells extended neurites directionally parallel to the collagen lines and field.

Figure 20:
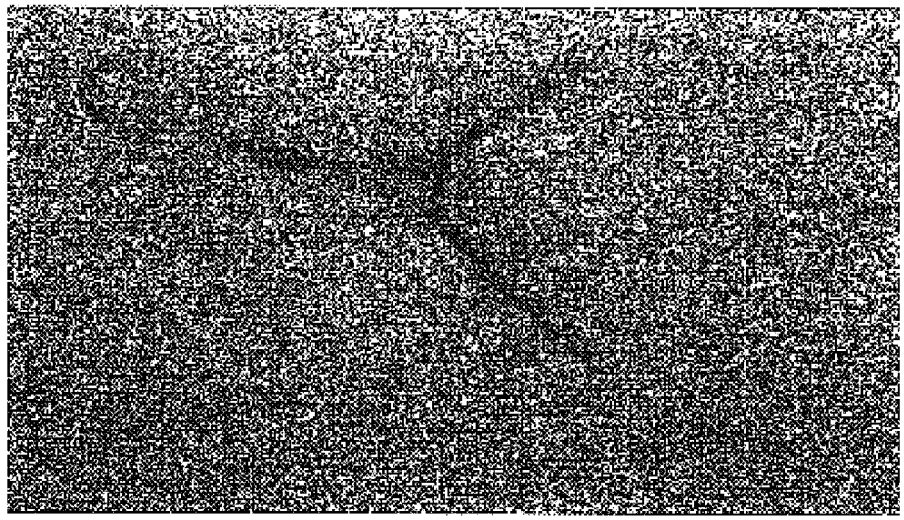
FIG. 20 is a photograph of neural crest cells on a columnar/void network film.

In another example of use of these columnar/void network deposited silicon films, the films were evaluated for their ability to promote the attachment, differentiation and proliferation of murine neural crest derived pluripotent stem cells. Neural crests were first derived and then plated on the thin film substrates that had been pre-treated with fibronectin. The neural crests adhered and crest cells migrated onto the surrounding substrate. Twenty-four hours after migration the crests were removed and the cells were allowed to differentiate and proliferate over the course of 2 weeks. Groups of cells which melanized and expressed neural and glial specific markers can be seen in these cultures, as may be noted FIG. 20.

(4) Electrical Contacts

Carrier injection is very important in supplying carriers in all electronic applications of molecules and organic material, e.g., it is important in the contact structures used for molecular electronic applications and for organic light emitting diodes (OLEDs). It is also important in the source/drain structures needed for molecular and organic thin film transistors (TFTs). Controlling the lateral spreading of self-assembling molecules or of any organic material when it is deposited on the surface for an OLED or TFT is also very important for device definition. This invention achieves both efficient carrier injection and enhanced device definition by using deposited columnar semiconductor materials. The columnar surface offers a multitude of carrier injecting structures, a matrix for immobilizing and thereby defining deposited films, and a large surface area open to surface functionalization treatments. The purpose of this element of our invention is twofold: (1) to improve the carrier injection efficiency into molecules (such as self assembling films) and into the organic materials; and (2) to enhance the definition of deposited materials.

Molecular electronics and organic thin film electronics are expected to provide cheaper, large area electronics than their silicon counterpart. Molecular electronics offers the possibility of cheap memory structures. Organic light emitting diodes offer the possibility of low cost displays on flexible substrates such as plastics. Molecular electronics and organic TFTs offer the possibility of inexpensive large area circuits for smart cards, smart sensor arrays, etc. All offer the possibility of printed light arrays and printed circuits formed by deposition steps such as self-assembling films or "ink jet" printing. However, OLEDs, OTFTs and molecular electronic structures have many problems. These possibilities are discussed in detail for the case of the OLEDs, specifically.

Figure 21:
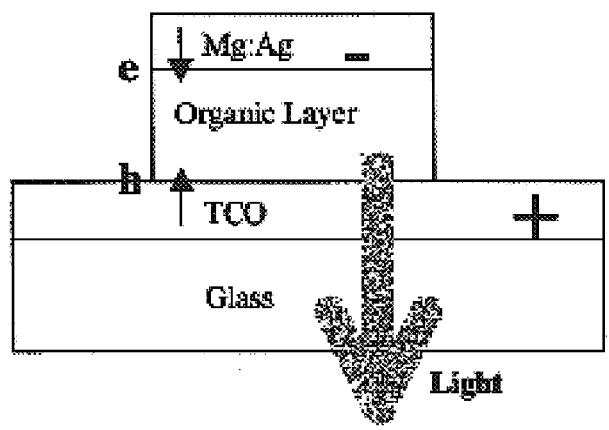
FIG. 21 is a schematic diagram of conventional OLED structure and contacting scheme.

OLEDs suffer from poor light emission efficiency and poor device definition. One of the reasons for poor efficiency is that many of these devices are based on the structure shown in FIG. 21.

In the light emission mode of this structure, a positive bias is applied to the transparent conductive oxide (TCO) while a negative bias is applied to the Mg:Ag electrode. In this biasing configuration holes are injected from the TCO while electrons are injected from the Mg:Ag electrode into the OLED material. These excess carriers meet in the OLED and the resulting electron-hole recombination produces light (photons) which passes through the TCO into the ambient. TCO is commonly used for the hole injection because of its high work function and its transparency. This structure is inherently limited, because the TCO is degenerately doped n-type material and hence does not possess enough holes to be an efficient hole injector. Hence, most of the OLEDs are hole limited. Problems such as these can also arise in OTFTs and molecular electronics.

In addition the lateral spreading of the organic material when it is deposited on the electrode surface can be of concern. This is because this spreading determines the smallest size a device (e.g., an OLED) can be made. In the case of OLEDs, for example, it consequently determines the pixel size and therefore the resolution. The lateral spreading is dependent on the properties of the organic fluid or self-assembling film material and the surface properties of the electrode.

The use of doped thin film void-column network materials as contacts for OLEDs, OTFTs and molecular electronics will enhance injection efficiency due to their multitude of contact points. They will also enhance structure definition due to their ability to immobilize deposited materials.

In the case of OLEDs to be specific, these materials can be used as either electrode. They can be used in place of TCO, or in place of the metal electrode. In the case of doped thin film void-column network silicon p-type material can be used, for example, in place of the TCO. The light emitted can be collected by making the low work function metal electrode very thin and using anti-reflection layers on the top of the metal, so that the light attenuation is minimal. These doped thin film void-column network materials can be fabricated using a high density plasma source as discussed previously.

The advantages of using the doped thin film void-column network silicon over conventional electrodes are manifold. The main advantages are:

(i) Improved carrier injection efficiency
(ii) Enhanced device definition
(iii) Ability to dope n-type or p-type.

The carrier injection efficiency is improved due to two reasons: columnar/void network material can be p-doped and thereby have larger number of holes than the conventionally used TCO. The field concentration at the column tips due to an applied bias on the electrode results in higher electric fields at the metal/organic interface and therefore higher injection.

The doped thin film void-column network silicon film is not continuous at its nucleating substrate surface, but is continuous at a short distance (~100 Å) from the surface. The columns all have the same perpendicular orientation to the substrate and essentially the same intercolumn (i.e., void) spacing. In addition the void region is continuous. These features mean that when the droplet of organic or self-assembling molecule material is placed on the surface of the film, the pillars (i.e., columns) that are sticking out will prevent the lateral spreading of the droplet. The droplet will be absorbed to some degree (which can be varied with surface treatments) into this matrix and the continuous nature of the void means droplet material entering into the void will also be continuous in all directions. The control of the surface by treatment with various chemicals such as Lewis acids has been demonstrated. The same techniques may be used to further control the surface and hence the spreading of the organic material.

(5) Sorting Structures

There is wide spread research into the use of porous polycrystalline silicon (poly-Si) structures for biomedical, sensor and analysis applications. Porous poly-Si possesses several properties, which make the material highly attractive for these applications. First, the ability to control pore size and topography within a dimensional range encompassing organic molecules and organisms makes the material very useful. Second, the ability to functionalize the surface with reactive, non-reactive, organic, organo-metallic and non-organic molecules allows the surface to be specified for reaction with an environment. Third, the material is well suited to interact with Si microelectronics.

Presently, the fabrication technique most widely used in the production of porous poly-Si is wet chemical etching and the electrochemical technique anodization. In this process conventional Si or thin film Si is exposed to a solution and etched as a current is passed through the material and solution.

As noted our nanostructured columnar/void deposited material differs from the "conventional" porous silicon in that it has a high, adjustable porosity with oriented columns and a controlled, uniform pore size where the pore size defined by the space between the columns. Unlike "conventional" porous silicon, our material can be deposited on any substrate—curved or flat—and at low deposition temperatures. The material can undergo oxidation, silicidation, etc. to change its physical and chemical properties. The pore size can also be adjusted by oxidation and etching, as needed. The columnar material need not be limited to silicon but other materials such as germanium are open to this deposition approach also.

Several biomedical applications for our deposited columnar/void network material have proven successful. For example, the surface of this material has successfully been passivated with functionalized organic molecules, which provides both a degree of protection for the material, making the surface physically more robust and chemically less reactive to wet etching, and allows us to specify reactions with nucleic acids, proteins and other organic or organo-metallic reagents. Chemical surface passivation in conjunction with microarray and nano-scale fabrication technology, allows the localization and sequestering of nucleic acids and proteins into or onto the intercolumnar space in an ordered and reproducible manner.

This material's highly sensitive amperometric response to intercolumnar solvent/ion concentration when a bias is applied allows the galvanic interrogation of the intercolumnar space for the presence of hybridized nucleic acids, proteins and other molecules. This approach would provide several improvements, on the order of magnitudes in size and sensitivity, over conventional nucleic acid hybridization arrays, which depend on sub-millimeter application technique and fluorescent detection technology. Other detection and quantification techniques such as MASF discussed above, atomic force microscopy and optical interference observation could augment or extend the application of this technology as a diagnostic tool.

The ability to attach nucleic acid and proteins to the surface and control the environment in the intrapore space makes nucleic acid amplification and in situ translation of nucleic acid a powerful application for research and clinical diagnostics.

(6) Other Applications (A) Modification of the Silicon Thin Film Surface

The surface of our columnar/void silicon may be modified by Lewis acid mediated reactions, lipid attachment, light mediated reactions or silinization reactions such as, hydrosilylation of alkynes and alkenes. A very broad range of chemical groups may be incorporated, allowing for tailoring of the interfacial characteristics of the material. The reaction can protect and stabilize our deposited silicon surfaces from atmospheric or direct chemical room-temperature photoluminescence.

(B) Sorting and Chromatography

The present films may also be used in applications such as gas chromatography, gel electrophoretic separation, isoelectric focusing, etc. These functions can be combined with the MASF function discussed above. Movement through the columnar or nanostructured columnar/void network structure can be controlled galvanically and specificity could be controlled by tailoring column size and/or in conjunction with surface modification using protein interaction, reactive enzymes, polar or non-polar molecules, anti-bodies, complementary nucleic acid and specifically tailored organic, organo-metallic and non-organic molecules.

The nanostructure columnar/void silicon network films can be used in nanoscale, microscale or macroscale applications, either as deposited or with post deposition chemical and physical modification including but not limited to: oxidation, nitration, silicide formation, silanization, antibody attachment, organic functional group attachment and electrochemically or chemically reduced releasing group attachment for separation of organic, molecular and atomic species by physical, chemical, magnetic or electrical interaction. Specifically, the separation, sorting, desalting and purification of proteins, peptides and nucleic acids by the application of DC or AC electrical fields can be achieved in structures utilizing continuous columnar/void silicon networks as both the primary means for the formation of the structures and as a coating or media with which the molecules will interact. In gas chromatographic (GC) applications, atomic or molecular gases may be separated by physical and chemical interaction with continuous columnar/void silicon network films deposited on GC channels.

(C) Cell and Body Structure Attachment

We have also established that the columnar/void network material has viability as a substrate for cell growth. Neural crest precursor cells when plated onto this material adhered, proliferated and began differentiation into cells of the expected neural, glia and elanocyte lineage. (See FIG. 20). When combined with micropatterning and the semiconductor nature of the material, it is possible to produce substrates for examining the inter and extracellular events involved in neuronal excitation, neuron-glia interaction, controlled or restricted growth. Also, this material has applications in vivo for tissue grafting including neuronal, glia, osteoblasts, osteoclasts, chondrocytes, kerotinocytes, melanocytes and epidermal cells.

(D) Adsorbance Medium

The nanostructured columnar/void silicon network films very strongly adsorb any contacting species. They adsorb liquid species and adsorb or condense gaseous species by physical absorption, capillary forces, and chemical and/or electronic interaction. The present films are useful as a "head space absorbance media" or a media, which is capable of absorbing analytes in the gaseous space above liquid. Temperature, chemical and physical surface modifications, chemical reactions, electric and magnetic fields can be used to selectively control the species that are absorbed or desorbed.

The present films can be used as a media for atomic and molecular absorbance or attachment. The nanostructured columnar/void silicon network films can absorb or be used as the substrate for attachment of proteins, peptides, nucleic acids, organic molecules and atomic species. These films with absorbed or attached molecules act as substrates for controlled, localized and detectable enzymatic, chemical or antigen/antibody interactions or reactions. Detection methods can include: MASF, DIOS, GC, fluorescence, electrical detection and color change assays.

(E) Integrated Capillary Chromatography/MASF Devices

Figure 22:
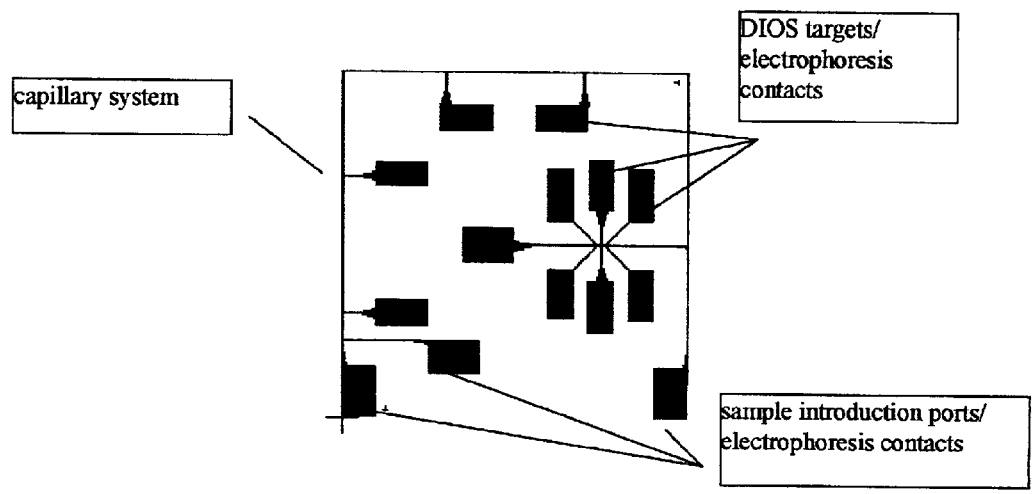
FIG. 22 is a schematic representation of an integrated capillary electrophoresis chip.

The subject film is so versatile that it can be used in the creation of a chip which integrates a system for electrophoresis capillary chromatography or some separation technique and subsequent desorption ionization of a sample. As shown in FIG. 22, a number of sample introduction ports/electrophoresis contacts are placed on the chip where the sample is initially deposited. A capillary system then connects these ports with a series of MASF targets/electrical contacts. By initiating electroosmosis, electrophoresis or other motive force the sample moves through the capillaries thereby separating the individual analytes in the sample and subsequently moving the analytes into separate MASF target contacts. The subject network film is placed on the contacts, both for introduction of the sample and for MASF analysis. Thus, the film facilitates not only adherence of the initial sample to the chip but also analysis of the separated analytes after electrophoresis. Use of the subject film in this integrated capillary electrophoresisMASF chip capacity demonstrates the adaptability of the films in combined applications.

What is claimed is:

1. A method for the analysis of a sample comprising:

(a) depositing a continuous film having optical properties and species adsorption properties essentially the same as optical properties and adsorption properties of bulk material of the continuous film;

(b) applying, after deposition of the continuous film, the sample to said deposited continuous film by either adsorption or directly to a surface of said deposited continuous film; and (c) analyzing the sample by matrix-less light desorption/ionization mass spectroscopy, after the sample has been applied to the deposited continuous film.

2. A method according to claim 1, wherein said sample is selected from the group consisting of organic chemical compositions, inorganic chemical compositions, biochemical compositions, drugs, drug metabolites, cells, cell material, micro-organisms, peptides, polypeptides, proteins, lipids, carbohydrates, nucleic acids, and combinations thereof.

3. A method for sample analysis according to claim 2, further comprising obtaining said sample from the group consisting of: a fluidic system, a microfluidic system, a nanofluidic system, a micro chromatographic system, a nano chromatographic system, a high-throughput isolation and preparation system, and combinations thereof.

4. A method according to claim 1, wherein said deposited film selected from the group consisting of: silicon, germanium, carbon, hydrogen and mixtures thereof.

5. A method according to claim 1, wherein the material used as said deposited continuous film is selected using criteria selected from the group consisting of light reflection, optical absorption, species absorption, analyte adsorption, ambient adsorption, analyte drying, and combinations thereof.

6. A method according to claim 1, further comprising, physically or chemically modifying said continuous film, surface functionalizing said continuous film, or patterning said continuous film prior to analyzing said sample.

7. A method according to claim 6, wherein patterning said continuous film is by: lithography comprising photolithography, probe, contact printing, imprinting, soft lithography; stamping; screen masking; printing or physically modifying said film or a subsequently positioned sample.

8. A method according to claim 6, wherein said physically or chemically modifying comprises reaction with or adherence with organic or inorganic compounds, cells, cell components, tissues, microorganisms and combinations thereof.

9. A method according to claim 1, wherein analyzing said sample is by laser desorption-ionization mass spectroscopy.

10. A method according to claim 1, wherein prior to analyzing said sample, a signal enhancing agent is integrated with said sample.

11. A method according to claim 10, wherein said signal enhancing agent is ammonium citrate.

12. A method according to claim 1, wherein applying said sample to said continuous film is by either (a) absorbing from a solid, liquid or gas; or (b) directly applying to the surface of said deposited continuous thin film as a solid or liquid, or combination thereof.

13. A method according to claim 12 wherein said sample is obtained from a separation means selected from at least one of the group consisting of: chemical, physical, and electrical separation means.

14. A method according to claim 13 wherein said separation means is selected from at least one of the group consisting of: liquid chromatography, gas chromatography, deposited thin film chromatography, size exclusion chromatography, affinity chromatography, gel electrophoresis, capillary or micro-capillary electrophoresis, and blotting.

15. A method according to claim 1, wherein said deposited continuous film is deposited on a substrate selected from the group consisting of silicon, semiconductors, insulators, glasses, plastics, polymers, metals, ceramics, and combinations thereof.

16. A method according to claim 1, wherein said deposited continuous film is deposited by chemical vapor deposition, physical vapor deposition, plasma enhanced chemical vapor deposition, hot wire deposition, nebulization, evaporation, sputtering, casting, spin coating, and combinations thereof.

17. A method according to claim 2, wherein said sample is a gas, liquid, solid, or combination thereof found in the general indoor environment, general outdoor environment, a process environment, and equipment environment.

18. A method according to claim 2, wherein said sample is a cell, plurality of cells, tissue, components thereof, and combinations thereof.

19. The method of claim 1 wherein said deposited continuous film comprises a semiconductor film.

* * * * *

UNITED STATES PATENT AND TRADEMARK OFFICE
CERTIFICATE OF CORRECTION

PATENT NO. : 6,794,196 B2  Page 1 of 1
APPLICATION NO. : 09/739940
DATED : September 21, 2004
INVENTOR(S) : Stephen J. Fonash et al.

It is certified that error appears in the above-identified patent and that said Letters Patent is hereby corrected as shown below:

In Col. 1, line 15, "F33615-98-1-5166" should read -- F33615-98-1-5164 --

Signed and Sealed this

Eighteenth Day of March, 2008

JON W. DUDAS
*Director of the United States Patent and Trademark Office*